US006855698B2

(12) United States Patent
Ruediger et al.

(10) Patent No.: US 6,855,698 B2
(45) Date of Patent: Feb. 15, 2005

(54) TOPOISOMERASE I SELECTIVE CYTOTOXIC SUGAR DERIVATIVES OF INDOLOPYRROLOCARBAZOLES

(75) Inventors: Edward H. Ruediger, Greenfield Park (CA); Mark G. Saulnier, Higganum, CT (US); Francis Beaulieu, Laprairie (CA); Carol Bachand, Candiac (CA); Neelakantan Balusubramanian, Madison, CT (US); Byron Hepler Long, Doylestown, PA (US); David B. Frennesson, Naugatuck, CT (US); Kurt Zimmermann, Durham, CT (US); B. Narasimhulu Naidu, Durham, CT (US); Karen Stoffan, Hartford, CT (US); Denis Robert St. Laurent, Newington, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 121 days.

(21) Appl. No.: 10/103,908

(22) Filed: Mar. 22, 2002

(65) Prior Publication Data

US 2003/0083271 A1 May 1, 2003

Related U.S. Application Data

(60) Provisional application No. 60/278,043, filed on Mar. 22, 2001.

(51) Int. Cl.$^7$ .......................... A01N 43/04; A61K 31/70
(52) U.S. Cl. ........................... 514/43; 514/42; 514/410; 536/18.7; 536/22.1; 536/27.1; 536/28.6
(58) Field of Search ............................ 514/42, 43, 410; 536/18.7, 22.1, 27.1, 28.6

(56) References Cited

U.S. PATENT DOCUMENTS

| 4,487,925 A | 12/1984 | Nettleton, Jr. et al. |
| 4,552,842 A | 11/1985 | Nettleton, Jr. et al. |
| 4,567,143 A | 1/1986 | Matson |
| 4,785,085 A | 11/1988 | Kaneko et al. |
| 5,043,335 A | 8/1991 | Kleinschroth et al. |
| 5,407,940 A | 4/1995 | Bisagni et al. |
| 5,468,849 A | 11/1995 | Lam et al. |
| 5,468,872 A | 11/1995 | Glicksman et al. |
| 5,475,110 A | 12/1995 | Hudkins et al. |
| 5,478,813 A | 12/1995 | Okaniski et al. |
| 5,498,611 A | 3/1996 | Bisagni et al. |
| 5,589,365 A | 12/1996 | Kojiri et al. |
| 5,618,809 A | 4/1997 | Barrabee et al. |
| 5,668,271 A | 9/1997 | Kojiri et al. |
| 5,674,867 A | 10/1997 | Tamaoki et al. |
| 6,037,468 A | 3/2000 | Wood et al. |

FOREIGN PATENT DOCUMENTS

| EP | 0 450 327 A1 | 10/1991 | |
| EP | 0602597 A2 | 12/1993 | |
| EP | 0545195 B1 | 11/1995 | |
| EP | 1101770 A | 5/2001 | |
| HU | 203758 B | 9/1991 | |
| HU | 211254 B | 11/1995 | |
| HU | 217611 B | 3/2000 | |
| WO | WO 89/07105 | 8/1989 | |
| WO | WO 95/30682 | 11/1995 | |
| WO | WO 96/04293 | 2/1996 | |
| WO | WO 96/11933 | 4/1996 | |
| WO | WO 98/07433 | * 2/1998 | .......... A61K/31/70 |
| WO | WO 99/02532 | 1/1999 | |

OTHER PUBLICATIONS

B. B. Shankar et al., *Tetrahedron Lett.* (1994), 35: 3005.
B. M. Stolz et al., *Tetrahedron Lett.* (1995), 36: 8543.
J. Anlzon et al., *Bioorg. & Med. Chem.* (1998), 6: 1597.
S.W. McCombie et al., *Bioorg. & Med. Chem. Lett.* (1993), 8: 1537.
C. Ballly et al, *Biochemistry* (1997), 36: 3917.
D. Von Hoff et al., *Cancer Chemother., Pharmacol.* (1994), 34 (suppl): 541.
T. Yoshinari et al., *Cancer Research* (1993), 53: 490.
T. Yoshinari et al., *Cancer Research* (1995), 55: 1310.
D.A. Scudiero et al., *Cancer Research* (1988), 48: 4827.
E.R. Perelra et al., *J. Med. Chem.* (1996), 39: 4471.
Greene and Wuts, Protective Groups in Organic Synthesis, $2^{nd}$ Ed., John Wiley and Sons and McOmie, New York, 1991.
J. L. Wood et al., *J. Am. Chem. Soc.* (1995), 117: 10413.
J. T. Unk et al., *J. Am. Chem. Soc.* (1996), 118: 2825.
R. Kobayoshi et al., *J. Am. Chem. Soc.* (1999), 121: 6501.
A. Mazur et al., *J. Org. Chem.* (1997), 62: 4471.
K. Nowak et al., *Roczniki Chem.* (1996), 43: 1953.
M. Gallant et al., *J. Org. Chem.* (1993), 58: 343.
M.S. Motawia et al., *J. Carbohydrate Chemistry* (1995), 14(9): 1279.
R.L. Halcomb et al., *J. Amer. Chem. Soc.* (1989), 111: 6661.
Nicolaou et al., *J. Amer. Chem. Soc.* (1989), 111: 6666.
S. F. Vice et al., *Bioorg. Med. Chem. Lett.* (1994), 4: 1333.
T. Hayashi et al., *Bioorganic And Medicinal Chemistry* (1997), 5(3): 497.
Weinreb et al., *Heterocycles* (1984), 21: 309.
Y.–H. Hsiang et al., *J. Biol. Chem.* (1985), 260(27): 14873.
Gonzalez, et al., *Farmacia Clinica* (1997), 14: 250.
Long, et al., *American Association for Cancer Research Proceedings* (1997), 38: 75.
Madden, et al., *Cancer Research* (1992), 52: 525.
O'Connor, et al., *Cancer Communications* (1990), 2: 395.
Pollack, et al., *Molecular Pharmacology* (1999), 56: 185.
Prudhomme, M., *Current Medicinal Chemistry* (2000), 7: 1189.

* cited by examiner

Primary Examiner—Patrick T. Lewis
(74) Attorney, Agent, or Firm—Kenneth W. Peist; Elliott Korsen

(57) ABSTRACT

The present invention relates to fluoro sugar and other sugar derivatives of indolopyrrolocarbazoles, their salts and hydrates, which exhibit selective topoisomerase I (topo I) activity, are useful in inhibiting the proliferation of tumor cells and exhibit an antitumor effect, as well as processes for their preparation.

45 Claims, No Drawings

TOPOISOMERASE I SELECTIVE CYTOTOXIC SUGAR DERIVATIVES OF INDOLOPYRROLOCARBAZOLES

RELATED APPLICATIONS

This application claims priority benefit under Title 35 §119(e) of U.S. provisional Application No. 60/278,043 filed Mar. 22, 2001.

FIELD OF THE INVENTION

The present invention relates to fluoro sugar and other sugar derivatives of indolopyrrolocarbazoles, their salts and hydrates, which exhibit selective topoisomerase I activity, are useful in inhibiting the proliferation of tumor cells and exhibit an antitumor effect, as well as processes for their preparation.

BACKGROUND

Topoisomerases are vital nuclear enzymes which function to resolve topological dilemmas in DNA, such as overwinding, underwinding and catenation, which normally arise during replication, transcription and perhaps other DNA processes. These enzymes allow DNA to relax by forming enzyme-bridged strand breaks that act as transient gates or pivotal points for the passage of other DNA strands. Topoisomerase-targeting drugs appear to interfere with this breakage-reunion reaction of DNA topoisomerases. In the presence of topoisomerase active agents an aborted reaction intermediate, termed a 'cleavable complex', accumulates and results in replication/transcription arrest, which ultimately leads to cell death.

The development of topoisomerase I (topo I) active agents therefore offers a new approach to the multi-regimental arsenal of therapies currently used in the clinic for the treatment of cancer. A recent article [*Cancer Chemother. Pharmacol* 1994, 34 (suppl), S41–S45] discusses topoisomerase I active compounds that are in clinical studies and these have been found to be effective clinical antitumor agents. These clinical candidates are structurally related to the alkaloid camptothecin (1). Other reports dealing with camptothecin analogs (*Cancer Commun.* 1990, 2, 395; *Farm. Clin.* 1997, 14, 250, 253, 256–258) have suggested a correlation between selective topoisomerase I inhibiting properties and potent antineoplastic activity in a variety of human tumors. In addition, certain cell lines which overexpress human topoisomerase I, including human colon carcinoma cells, have been demonstrated to be hypersensitive to camptothecin (*Cancer Research* 1992, 52, 525).

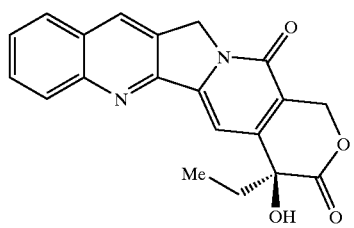

1

A recent review highlights some of the non camptothecin topoisomerase I active agents (Expert Opin. Ther. Pat. 10:635–666, 2000). Further, indolo[2,3-a]carbazole derivatives related to the Rebeccamycin class, such as NB-506, are disclosed (EP Appl. 0 545 195 B1 and 0,602,597 A2; *Cancer Research* 1993, 53, 490–494; ibid 1995, 55, 1310–1315) and claimed to exhibit antitumor activity. However, unlike camptothecin which acts as a selective topo I poison, these derivatives have been reported to be non-selective, exhibiting additional biological effects, such as DNA intercalation (*Cancer Research* 1995, 55, 1310), tyrosine kinase activity (*Molecular Pharmacol.* 1999, 56, 185–195) and topoisomerase II activity (*Proc. AACR* 1997, 38, 75). Indolo[2,3-a]carbazole alkaloids such as rebeccamycin (U.S. Pat. Nos. 4,487,925 and 4,552,842) and its water-soluble, clinically-active analog, 6-(2-diethylaminoethyl) rebeccamycin (U.S. Pat. No. 4,785,085), are useful antitumor agents which target DNA. Related indolocarbazoles are also disclosed (WO 9530682) and claimed to exhibit antitumor activity.

Furthermore, fluoroindolocarbazoles such as those described in WO 98/07433 are antineoplastic agents with topoisomerase I inhibitory activity. U.S. Pat. No. 5,468,849 discloses certain fluororebeccamycin analogs as useful antitumor agents, along with a process for their production by fluorotryptophan analog feeding of a rebeccamycin-producing strain of *Saccharothrix aerocolonigenes*, preferably *Saccharothrix aerocolonigenes* C38,383-RK2 (ATCC 39243).

More recently Prudhomme, et al. report a series of indolocarbazoles derived from rebeccamycin which all display a so-called resistance index below 20 (*Current Medicinal Chemistry* 2000, 7, 1189). The resistance index was defined as $IC_{50}$ P388CPT5/$IC_{50}$ P388, where these $IC_{50}$'s are measures of the antiproliferative activities against murine P388CPT5 leukemia cells resistant to camptothecin and parental P388 cells, respectively.

Despite these examples, there remains a need for novel and potent cytotoxic compounds useful for selectively inhibiting topoisomerase I activity, thereby being useful as anticancer agents.

SUMMARY OF THE INVENTION

The present invention relates to fluoro sugar and other sugar derivatives of substituted indolopyrrolocarbazoles, their salts and hydrates, which exhibit topoisomerase I (topo I) activity, are useful in inhibiting the proliferation of tumor cells and exhibit an antitumor effect, as well as processes for their preparation More specifically, the instant invention provides compounds of formula I

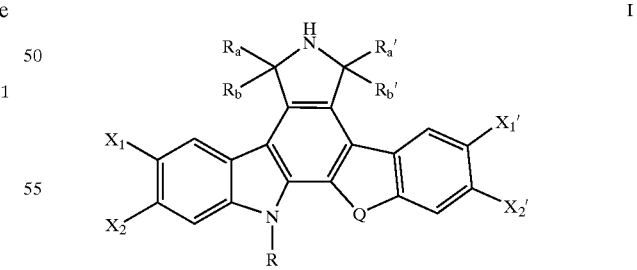

I having a topoisomerase I selectivity index of greater than about 100; its enantiomers, diastereomers, pharmaceutically acceptable salts, hydrates, prodrugs and solvates thereof; wherein $R_a$ and $R_b$ are independently selected from the group consisting of H and O, provided that when O is selected $R_a$ and $R_b$ are taken together to form O; $R_a'$ and $R_b'$ are independently selected from the group consisting of H and O, provided that when O is selected $R_a'$ and $R_b'$ are taken together to form O; $X_1$, $X_1'$, $X_2$ and $X_2'$ are each independently selected from the group consisting of F, Br and H; Q is selected from the group consisting of NH, S and O; and R is a substituted hexose group.

The invention also provides a method for treating a condition via modulation of topoisomerase I comprising administering to a mammalian species in need of such treatment an effective amount of at least one compound of formula I, as defined above.

DETAILED DESCRIPTION OF THE INVENTION

The present invention includes fluoro sugar and other sugar derivatives of indolopyrrolocarbazoles of formula (I), as defined above. These compounds and their pharmaceutically acceptable salts and hydrates exhibit selective topoisomerase I (topo I) activity, are useful in inhibiting the proliferation of tumor cells and exhibit a significant antitumor effect. Most importantly, the instant invention describes topo I active compounds, related to compounds disclosed in WO 98/07433 and co-pending U.S. application, Ser. No. 08/914566 (both herein incorporated by reference), which display a surprising and unexpected selectivity index when evaluated for cytotoxicity in certain cell lines which express normal levels of topo I required for cell proliferation, compared with cell lines that are deficient in or underexpress topo I. Said "selectivity index" (R/S) was generated by dividing the cytotoxic $IC_{50}$ of a particular compound against a camptothecin-resistant murine leukemia cell line, P388/CPT45, by the $IC_{50}$ generated when using the parent P388 cell line. Compounds that are structurally closely related to the indolopyrrolocarbazoles previously identified as having topo 1 activity, as well as reference agents known to exhibit cytotoxic effects as a result of other mechanisms of action, have been shown to exhibit a wide and unpredictable range of selectivity indices (R/S) (*Proc. AACR* 1997, 38, 75). A level of selectivity was judged to be advantageous and beneficial in, for example, modulating potential undesirable side effects and/or toxicity. The compounds of the present invention were selected from compounds generically disclosed in WO 98/07433 and co-pending U.S. patent application, Ser. No. 08/914566, on the basis of an unexpected and unpredictable selectivity index (see Table I and II). As can be seen from Table I and II, structurally closely related analogs which may exhibit topoisomerase I activity and inhibition of cell proliferation, as measured by the methods given below, still vary in their topoisomerase I selectivity. Simple changes in the substitution of the sugar portion or the indolopyrrolocarbazole portion of the present invention will change the selectivity. This change in selectivity is not predictable by one skilled in the art. The camptothecin class of compounds, which also exhibits topo I activity and selectvity, does not exhibit such unpredictable selectivity. As demographic changes occur in the treatment population, identifying selective agents for tailored therapy will be a key factor for providing an acceptable therapeutic index and hence increased safety and tolerability. In sum, nothing in the reported literature would suggest or teach that the selected indolocarbazoles of the present invention might be expected to exhibit a camptothecin-like topoisomerase I selectivity and antitumor activity.

In general, the instant invention comprises compounds of formula I,

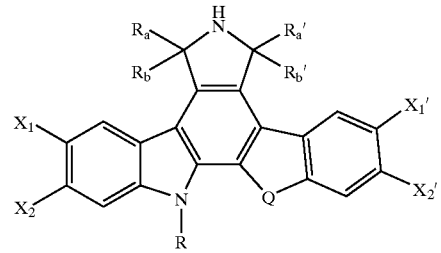

I having a topoisomerase I selectivity index of greater than about 100; its enantiomers, diastereomers, pharmaceutically acceptable salts, hydrates, prodrugs and solvates thereof. $R_a$ and $R_b$ may either be H or taken together as O. Similarly, $R_a'$ and $R_b'$ may are either be H or taken together as O. $X_1$, $X_1'$, $X_2$ and $X_2'$ are each independently selected from the group consisting of F, Br and H. Q is selected from the group consisting of NH, S and O. Finally, R is a substituted hexose group.

In a preferred embodiment, $X_1$ is F; $X_1'$ is selected from the group consisting of F and Br; and, $X_2$ and $X_2'$ are selected from the group consisting of F and H.

In another preferred embodiment, $X_1$ and $X_1'$ are F; $X_2$ and $X_2'$ are H; and Q is NH.

In yet another preferred embodiment, $X_1$ and $X_1'$ are F; $X_2$ and $X_2'$ are H; Q is NH; $R_a$ and $R_b$ are taken together as O; $R_a'$ and $R_b'$ are H; and said substituted hexose group is

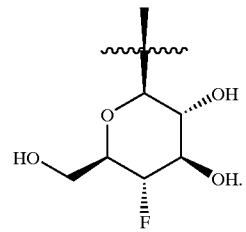

In still yet another preferred embodiment, $X_1$ and $X_1'$ are F; $X_2$ and $X_2'$ are H; Q is NH; $R_{a\text{-}}'$ and $R_{b\text{-}}'$ are taken together as O; $R_a$ and $R_b$ are H; and said substituted hexose group is

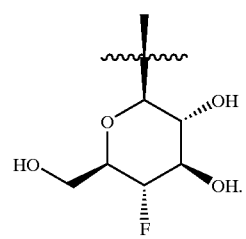

In yet another preferred embodiment, the invention is compound

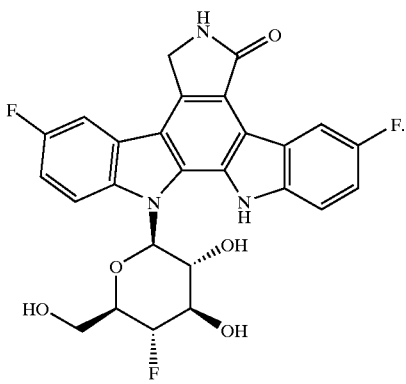

In another preferred embodiment, the invention is the compound

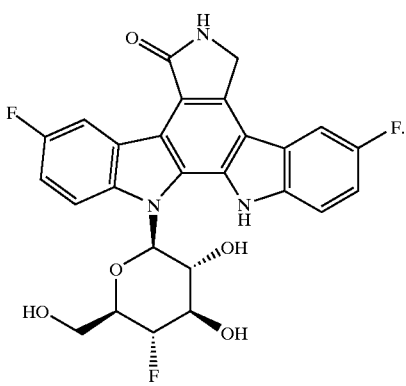

In still yet another preferred embodiment, the invention is the compound

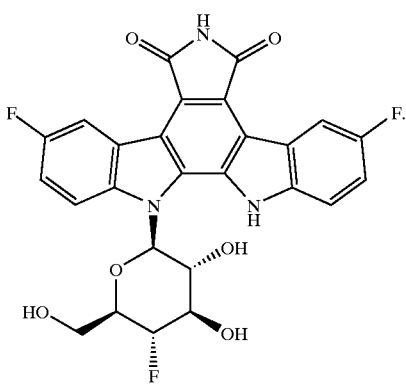

The invention also provides a method for treating a condition via modulation of topoisomerase I comprising administering to a mammalian species in need of such treatment an effective amount of at least one compound of formula I, as defined above. In a preferred embodiment, the condition associated with topoisomerase I is cancer. In another preferred embodiment, the method further comprises administering to said mammalian species at least one other anti-cancer agent in combination (sequentially or simultaneously) with at least one compound of formula I.

It is to be understood that the present invention includes any and all possible stereoisomers, geometric isomers, diastereoisomers, enantiomers and anomers, unless a particular description specifies otherwise. The compounds of this invention can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group can exist in the form of an alkali metal salt such as, for example, a potassium salt and a sodium salt; an alkaline earth metal salts such as, for example, a magnesium salt and a calcium salt; and salts with organic bases, such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those of ordinary skill in the pharmaceutical arts. The compounds can be administered alone but generally will be administered with a pharmaceutical carrier selected upon the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

DESCRIPTION OF THE SPECIFIC EMBODIMENTS

Representative procedures for the preparation of Formula (I) compounds are illustrated in Schemes 1–9.

SCHEME 1:
Preparation of Example 22 and 28
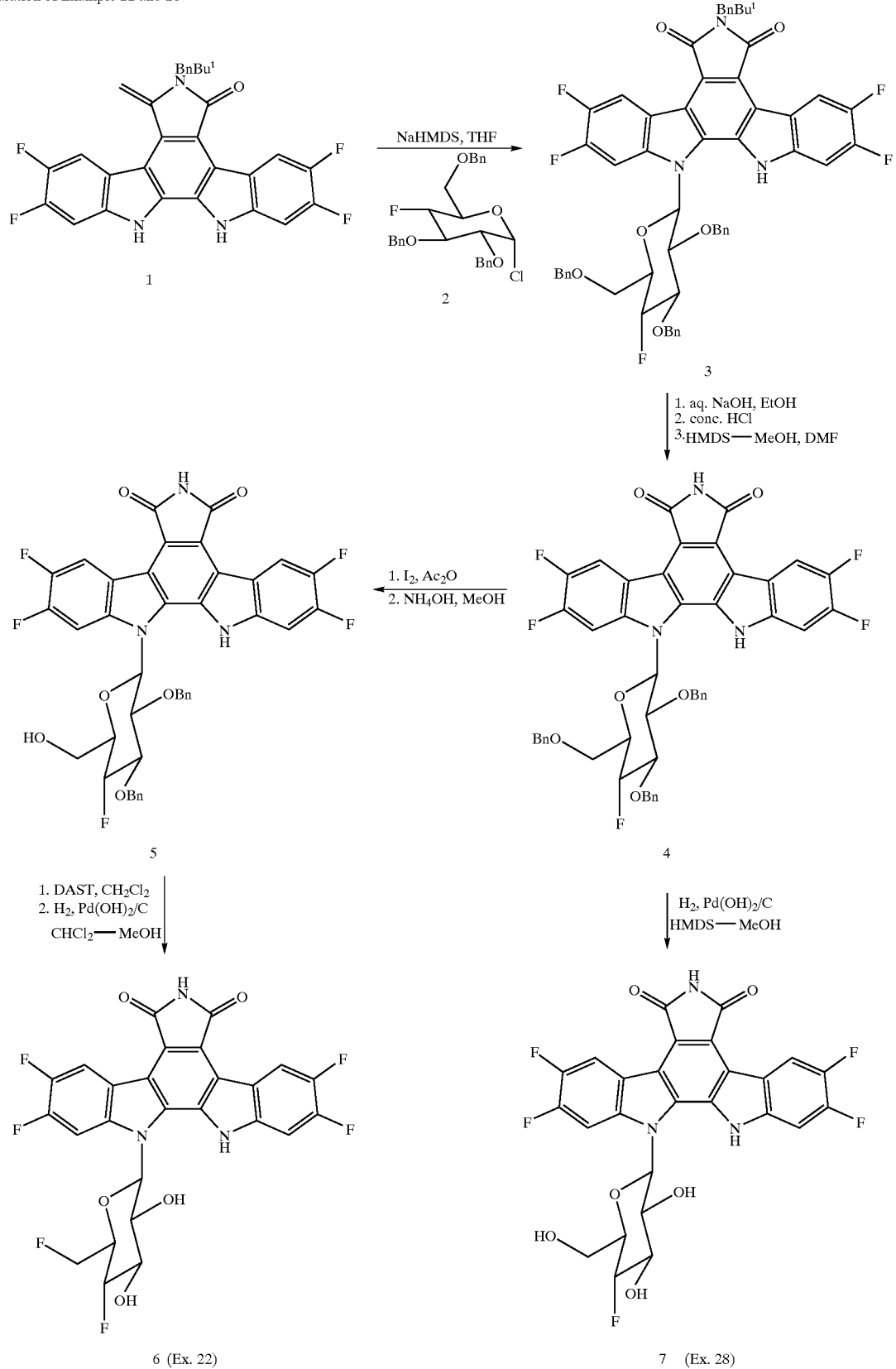

SCHEME 2:
Preparation of Example 17
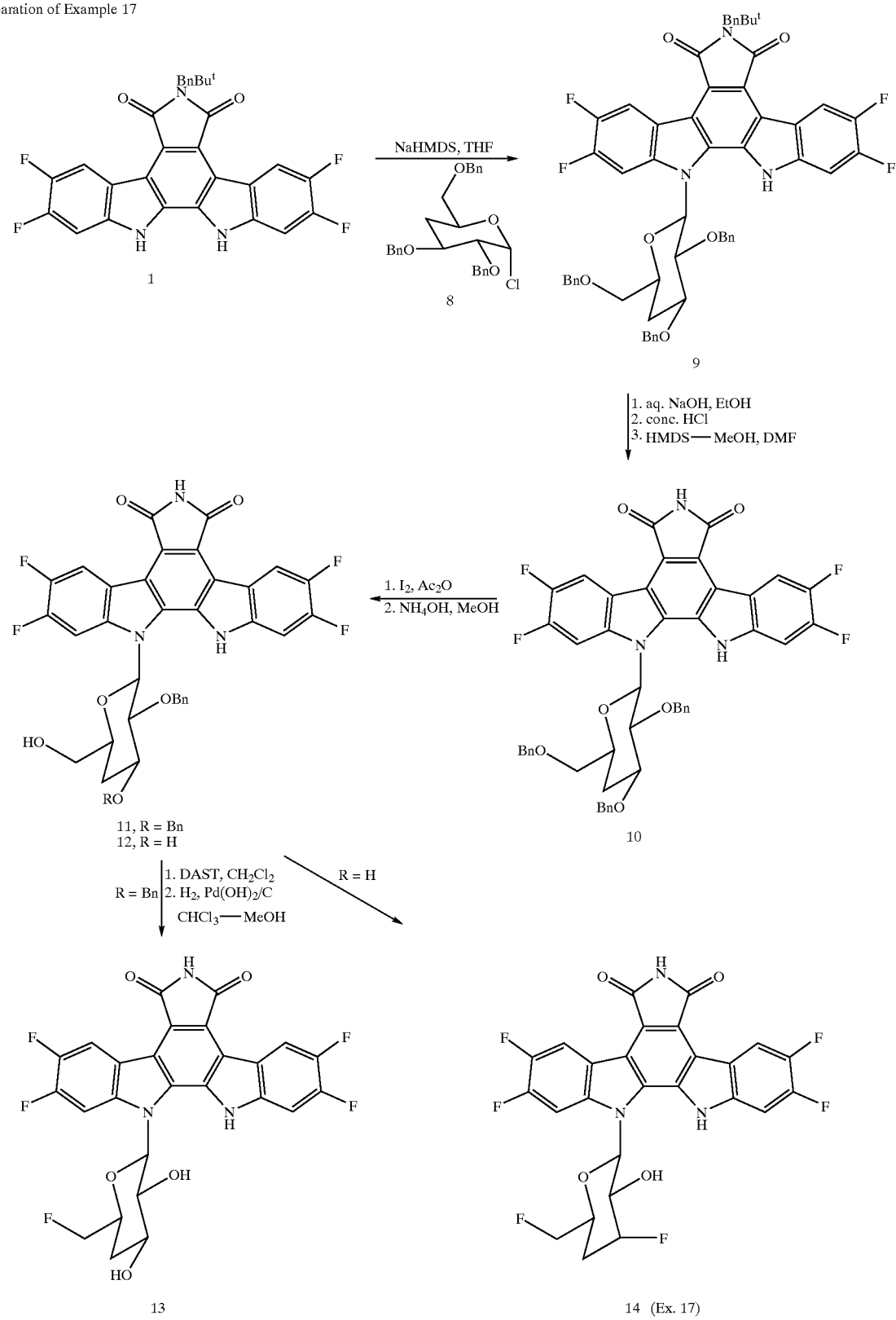

SCHEME 3:
Preparation of Example 11 and Example 31
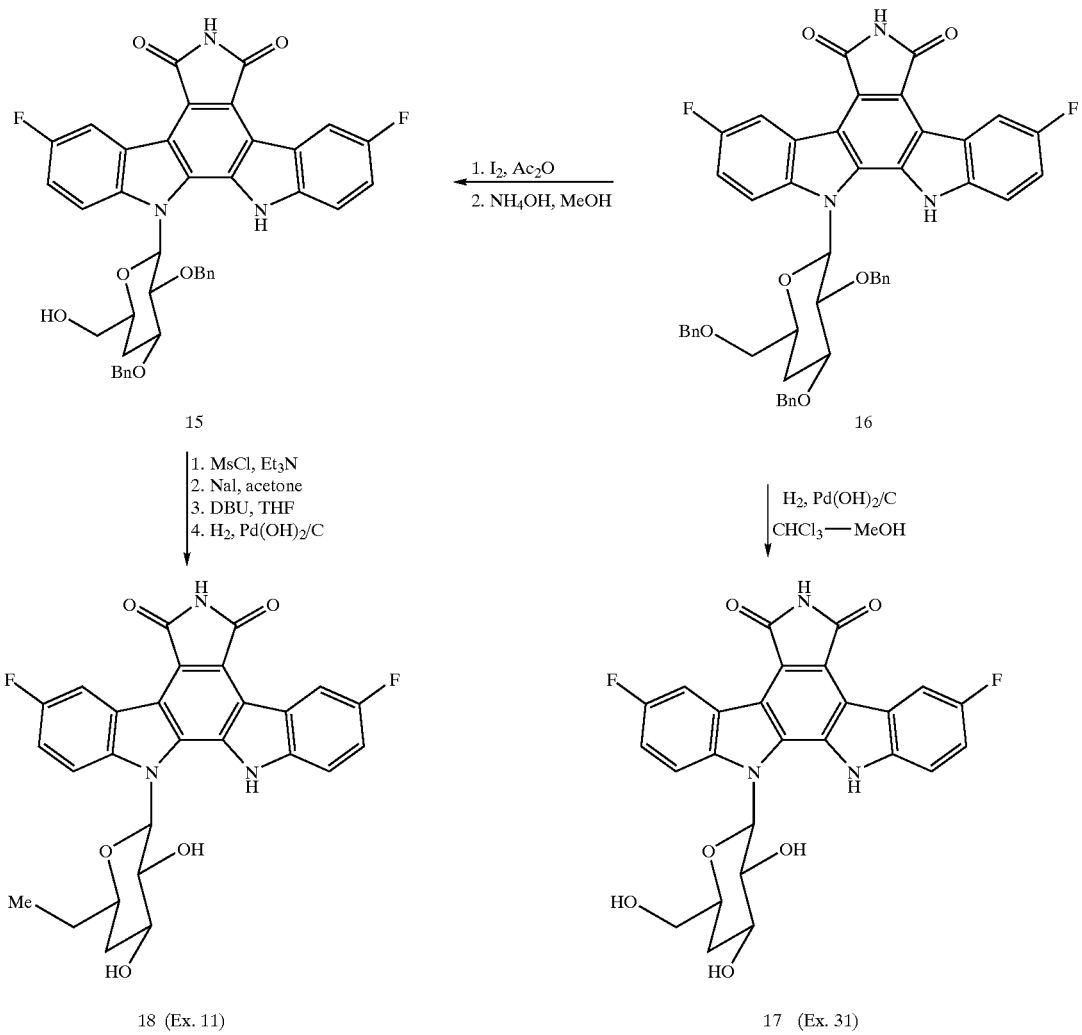
SCHEME 4:
Preparation of Example 5
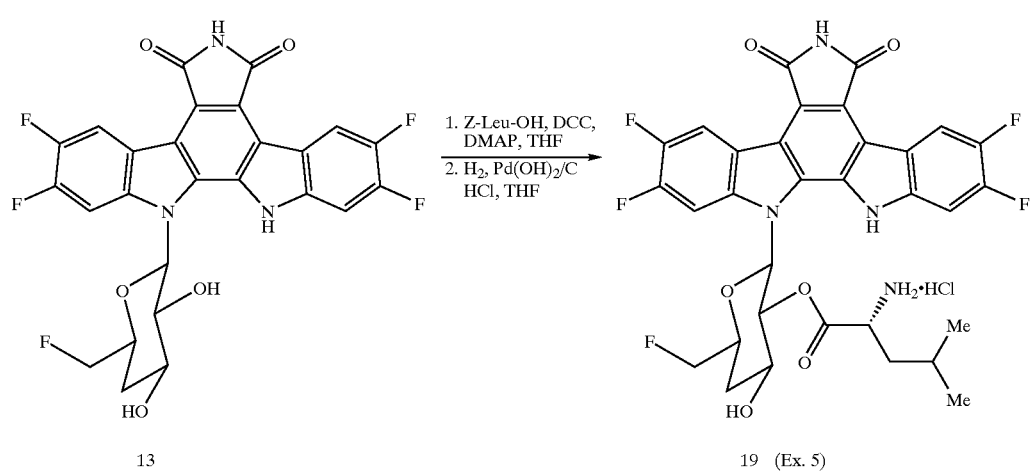

SCHEME 5:
Preparation of Example 18 and Example 29
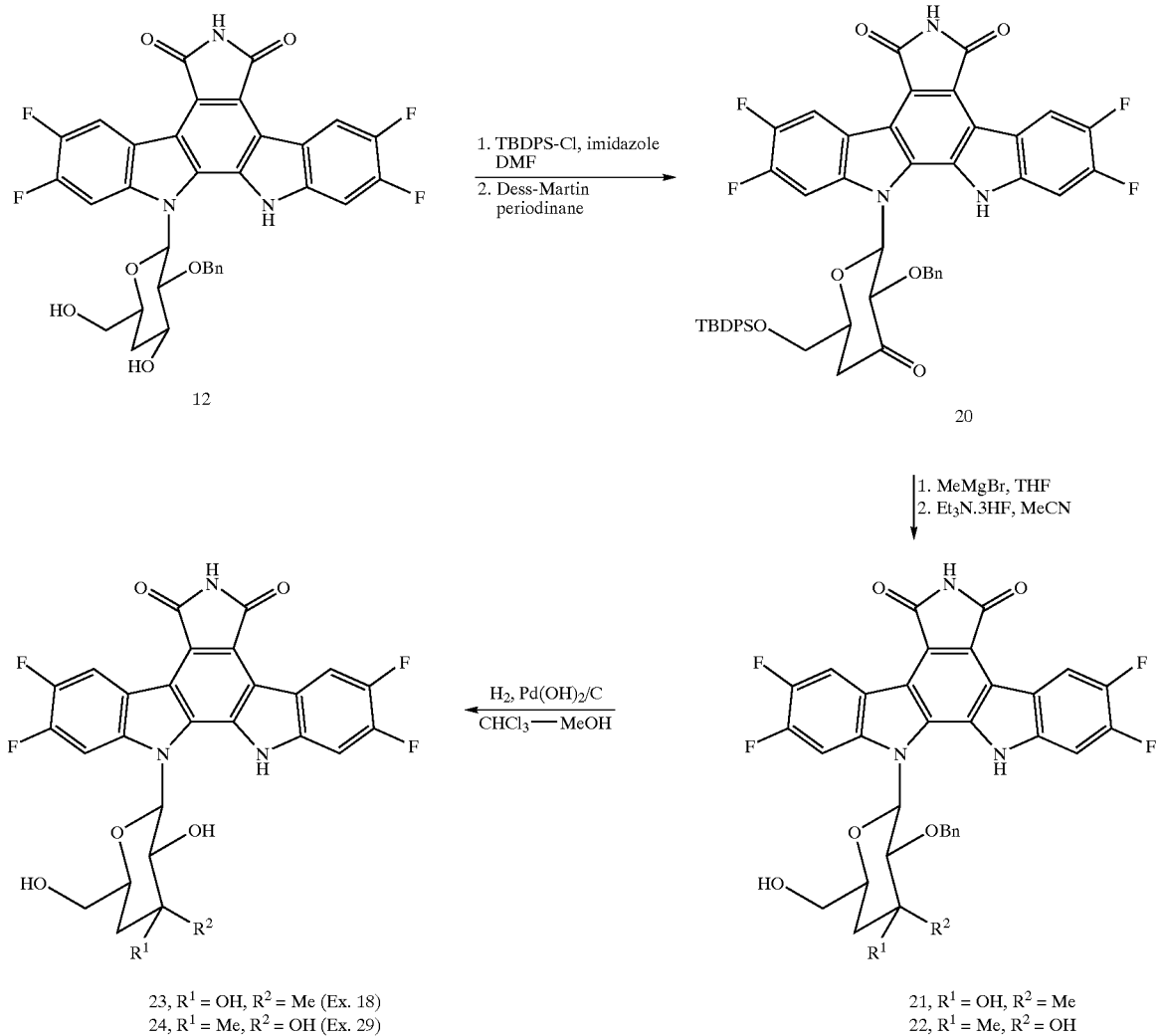
SCHEME 6:
Preparation of Example 8
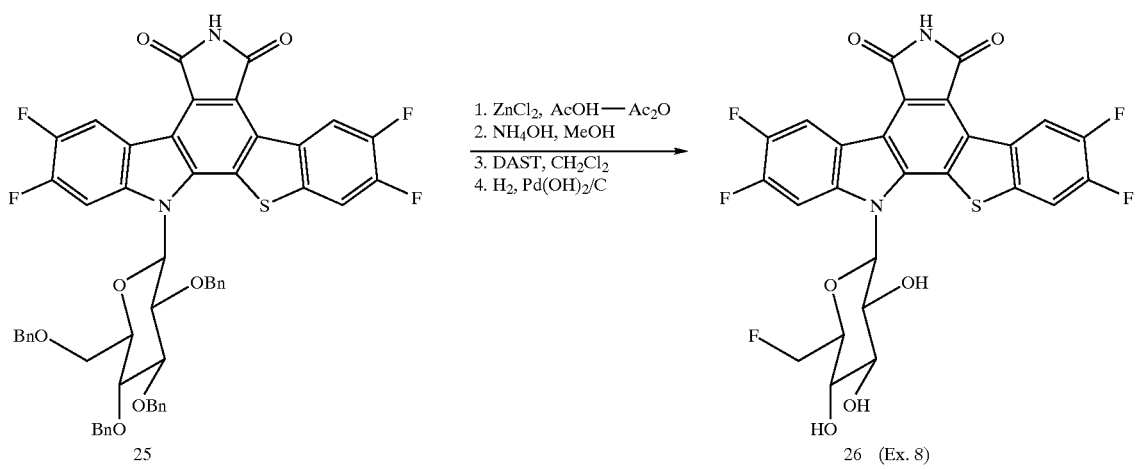

SCHEME 7:
Preparation of Example 23

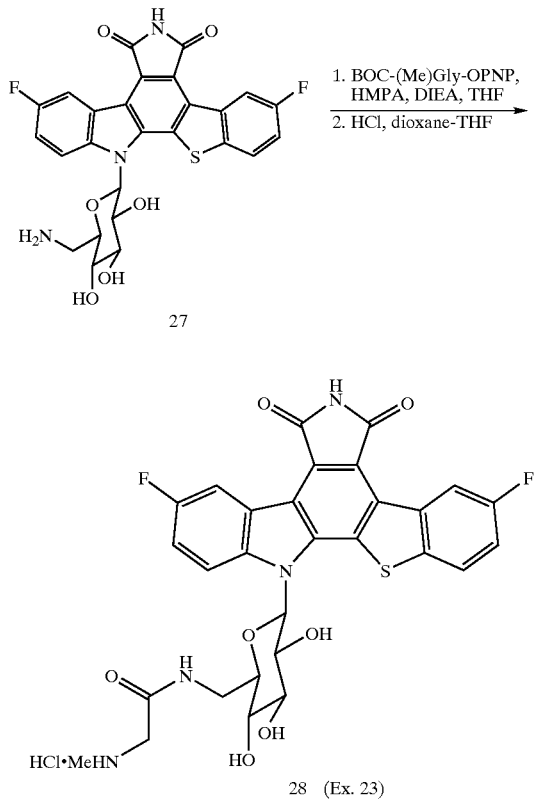

SCHEME 8:
Preparation of Example 12

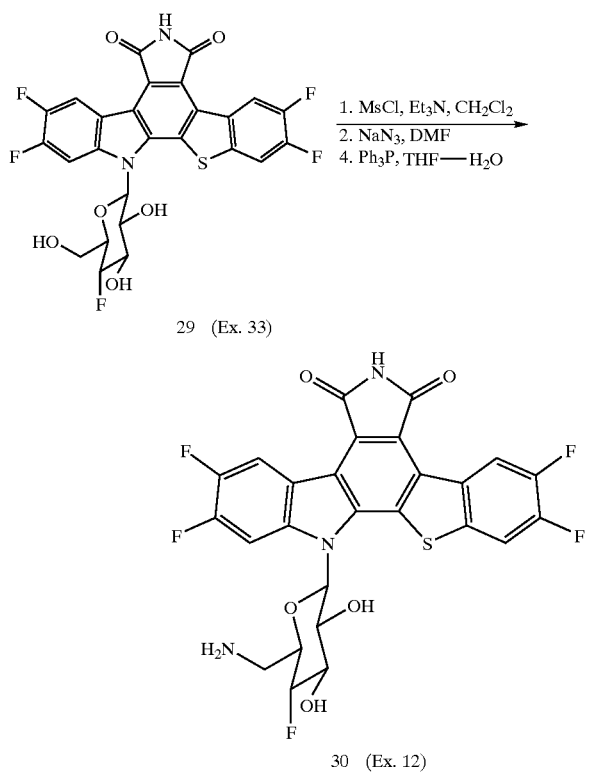

SCHEME 9:
Preparation of Example 32 and 34

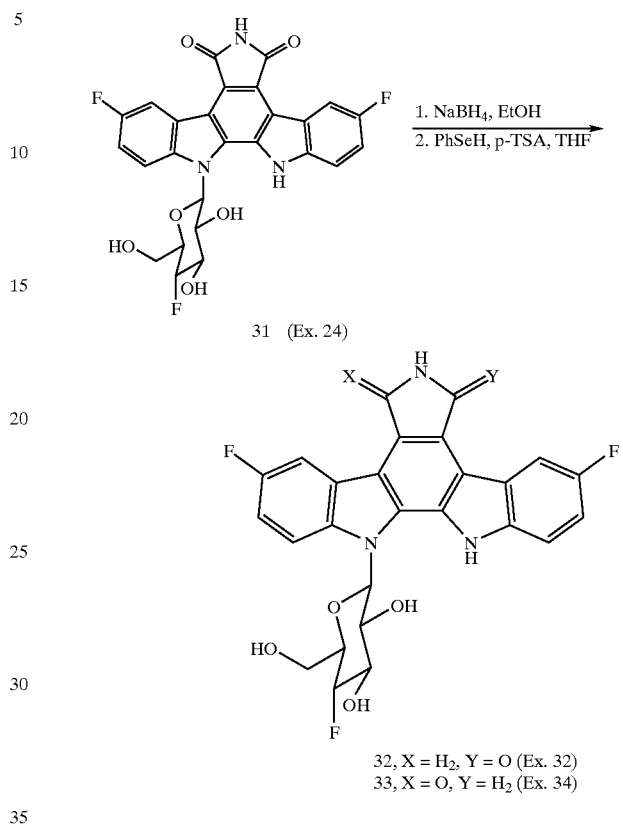

Fluorosugar substituted derivatives of fluoroindolocarbazoles were conveniently prepared as shown in a representative procedure in Scheme 1. A fluoroindolocarbazole core (1) was glycosylated by deprotonation with a suitable base, such as sodium hexamethyldisilazane, and subsequent treatment with a chlorosugar, such as the 4-fluoroglucopyranoside 2, to give the N-glycosylindolocarbazole 3. Deprotection of the imide moiety of perbenzylated glycosides such as 3 was done by base-induced hydrolysis, followed by acidification to give an intermediate anhydride. The latter was conveniently converted to an imide (e.g., 4) using a suitable amine, such as that provided by reaction with a mixture of hexamethyldisilazane and methanol in dimethylformamide (cf. P. D Davis, R. A. Bit Tetrahedron Lett. 1990, 31, 5201). Removal of the benzyl protecting groups could then be done using a conventional procedure involving hydrogenolysis over Pearlman's catalyst (20% $Pd(OH)_2$ on charcoal) to give a fully deprotected glycoside (7). Alternatively, a partially deprotected glycoside (5) could be prepared by treatment of the corresponding perbenzylated glycoside (4) with iodine in acetic anhydride (cf. K. P. R. Kartha, R. A. Field Tetrahedron 1997, 53, 11753), followed by hydrolysis of the intermediate acetate. Subsequent treatment of this selectively deprotected glycoside with the well-known fluorinating agent DAST [(diethylamino)sulfur trifluoride], followed by debenzylation as before, then gives a fluorinated glycoside (6).

A series of deoxyglycosides could be prepared in analogous fashion as shown in Scheme 2. In this case, a judicious choice of reaction conditions was used to convert a perbenzylated glycoside (10) to a readily separable mixture of dibenzyl (11) and monobenzyl (12) glycosides. Treatment of 11 with DAST and subsequent deprotection, as before, then gave a fluorodeoxyglucoside (13). Identical treatment of the diol 12 afforded a difluorodeoxyalloside (14). Related deoxyglycosides were prepared as shown in Scheme 3. Hydrogenolysis of 16, as described before, gave a monodeoxyglycoside (17). Alternatively, a judicious choice of reaction conditions furnished a partially deprotected glycoside (15), using the previously described approach. The resulting primary alcohol could then be activated, for example as its mesylate and subsequently the corresponding iodide, and induced to undergo elimination of the element of HI using a suitable amine base, such as 1,8-diazabicyclo[5.4.0]undec-7-ene (DBU), to give a vinyl ether. A final hydrogenolysis step then afforded a dideoxyglycoside 18.

Unprotected glycosides prepared in the foregoing ways could also be selectively functionalized as shown in Scheme 4. Coupling of a fluoroglycoside (13) with a protected amino acid, such as N-benzyloxycarbonyl-L-leucine, could be done selectively under standard esterification conditions using, for example, dicyclohexylcarbodiimide (DCC) and 4-dimethylaminopyridine (DMAP) to effect the reaction. Subsequent deprotection under standard hydrogenolysis conditions then gave an amino acid ester (19). Similarly, amino acid amides could be prepared as shown in Scheme 7. Reaction of an aminoglycoside (27) with the p-nitrophenyl ester of a protected amino acid, such as that of N-tert-butyloxycarbonyl-N-methylglycine, under standard peptide coupling/deprotection conditions afforded the amide 28.

Alkylated glycosides could also be prepared as shown in Scheme 5. A previously prepared diol (12) was selectively protected as its monosilyl ether using standard silylating conditions, such as treatment with tert-butyldiphenylchlorosilane in the presence of imidazole, using a suitable solvent such as dimethylformamide. Subsequent oxidation of the remaining unprotected hydroxy substituent was then conveniently done using Dess-Martin periodinane as oxidizing agent to give an intermediate ketone (20). Reaction of 20 with a Grignard reagent such as methylmagnesium bromide and subsequent removal of the silyl protecting group, using triethylamine trihydrofluoride, gave a readily separable mixture of the two tertiary alcohols, 21 and 22. The latter two compounds were then individually deprotected as before to give the methylglucoside 23 and the methylalloside 24.

Monofluorinated glycosides of a variety of aromatic cores related to 1 could also be prepared as shown in Scheme 6, using an analogous approach and reaction conditions already described in Scheme 1.

Selected fluoroglycosides such as 29 could also be further functionalized as shown in Scheme 8. Selective activation of the primary alcohol as its mesylate and subsequent displacement using sodium azide in dimethylformamide gave the corresponding azide. Reduction of the azide under Staudinger reaction conditions then gave the amine 30.

The aromatic core of selected fluoroindolocarbazoles was also readily reduced as shown in Scheme 9. The imide moiety was first reduced by treatment with a reducing hydride, such as sodium borohydride, with further reduction using benzeneselenol to give essentially equal amounts of the corresponding lactams 32 and 33, as a separable mixture.

The pharmacological properties of the compounds of this invention may be confirmed by a number of pharmacological assays. The exemplified pharmacological assays which follow have been carried out with the compounds or their salts according to the invention.

Topoisomerase I Activity (In Vitro)

Topoisomerase I activity was measured as described below. The procedure for assaying compound-induced, topoisomerase I-mediated single strand breaks in DNA was essentially that described by Hsiang, et al., (*J. Biol. Chem.* 1985, 260, 14873–14878). Samples dissolved in 100% DMSO as either 10 $\mu$M or 10 mg/ml solutions, unless otherwise stated, were diluted in Tris-EDTA buffer. Marine bacteriophage PM2 DNA (Boehringer Mannheim) was also diluted in Tris-EDTA buffer to a concentration of 0.02 $\mu$g/$\mu$l. Different dilutions of the compound being evaluated were mixed with diluted DNA and this mixture was added to 1000 unit (one unit of enzyme activity is defined as the amount capable of relaxing 100 ng of supercoiled DNA in approximately 30 minutes at 37° C.) aliquots of purified human topoisomerase I (Topogen) in 2× reaction buffer to start the reaction. The compound-DNA-enzyme mixture was incubated for 30 minutes at 37° C. before stopping the reaction with warm stop buffer containing sodium dodecyl sulfate and proteinase K (Sigma). These mixtures were allowed to incubate at 37° C. for another 10 minutes, at which time the mixtures were removed from the waterbath and extracted with a 24:1 mixture of chloroform/isoamyl alcohol. Following centrifugation, aliquots of the aqueous phases were placed in wells of a 0.9% agarose (SeaKem) gel in Tris-borate buffer containing 0.5 $\mu$g/ml of ethidium bromide and subjected to electrophoresis for 15 hours to separate the different topological isomers and nicked and broken DNAs. After destaining the gel in water, the ethidium bromide stained DNA reaction products were visualized by exposing the gel to UV irradiation. Negatives of the photographs of the irradiated gels were scanned with a densitometer and areas under the peaks were calculated in order to obtain percent single strand DNA break formation for each sample. A median effective concentration ($EC_{50}$) was obtained for each compound by interpolation between points of the resulting dose-effect curve which defines the potency of the compound for its effect in inducing topoisomerase I-mediated single strand breaks in DNA. The topoisomerase I activities for certain compounds of the present invention are shown below in Table I.

In Vitro Cell-Based Cytotoxicity Activity

The proliferation inhibition activity against the murine P388 cell line was measured as follows. Evaluation of a soluble tetrazolium/formazan assay for cell growth and drug sensitivity in culture, using human and other tumor cell lines, was done according to the procedure described in *Cancer Res.* 1988, 48, 4827–4833. Cells were plated at 4000 cells/well in 96 well microtiter plates and 24 h later drugs were added and serially diluted. The cells were incubated at 37° C. for 72 h, at which time a tetrazolium dye, XTT, containing phenazine methosulfate was added. A dehydrogenase enzyme in live cells reduced the XTT to a form that absorbs light at 450 nm, which could be quantitated spectrophotometrically. The greater the absorbance the greater the number of live cells. The results are expressed as an $IC_{50}$, which is the drug concentration required to inhibit cell proliferation (i.e., absorbance at 450 nm) to 50% of that of untreated control cells.

Similarly, P338 murine leukemia cells were maintained in RPMI 1640 supplemented with 20% fetal bovine serum and 10 $\mu$M 2-mercaptoethanol. A camptothecin resistant subline, P388/CPT45, was selected for resistance to camptothecin and is over 1000-fold resistant to this compound (Woessner, et al. *Oncol. Res.* 1992, 4, 481–488). The mechanism of resistance has been shown to be reduced levels of topoisomerase I.

In vitro cytotoxicity was assessed in tissue culture cells by MTS (3-(4,5-dimethylthiazol-2-yl)-5-(3-carboxymethoxyphenyl)-2-(4-sulphenyl)-2H-tetrazolium, inner salt) assay (Riss and Moravec, *Mol. Biol. Cell* 1992, 3 (Suppl.), 184a). Cells were plated at 8,000 cell/well in 96 well microtiter plates and 24 hours later serial dilutions of the test compounds were made and added to the cells. The cells were incubated at 37° C. for 72 hours, at which time the tetrazolium dye, MTS at 333 μg/ml (final concentration), in combination with the electron coupling agent phenazine methosulfate at 25 μM (final concentration) was added. A dehydrogenase enzyme in live cells reduces the MTS to a form that absorbs light at 492 nm which can be quantitated spectrophotometrically. The greater the absorbance the greater the number of live cells. The results are expressed as an $IC_{50}$, which is the drug concentration required to inhibit cell proliferation (i.e., absorbance at 492 nm) to 50% of that of untreated control cells.

The cytotoxic activity for certain compounds of the present invention, in both parental P388 and the camptothecin-resistant P388/CPT45 cell lines are shown below in Table I.

Selectivity Index (R/S)

The selectivity index (R/S) is defined as the ratio obtained by dividing the $IC_{50}$ value obtained using P388/CPT45 cells by that obtained using parental P388 cells. The R/S ratios used to determine the relative topo I selectivity of selected compounds of this invention are shown below in Table I.

By way of comparison, the topo I activity, cytotoxicity and selectivity index of closely related non-selective, topo I-active fluoroindolocarbazoles are shown below in Table II.

TABLE I

In Vitro Topoisomerase I Activity and Cytotoxicity of Topoisomerase-I Selective Analogs against Murine P388 Leukemia Cells.

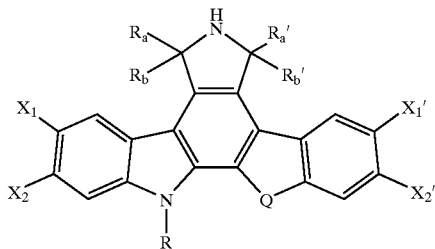

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I[§] $EC_{50}$ (μM) | P388[†] $IC_{50}$ (μM) | Selectivity Index R/S[‡] |
|---|---|---|---|---|---|---|---|---|---|
| 1 | F | F | H | H | NH | | 0.05 | 0.057 | 101.7 |
| 2 | F | F | H | H | NH | | 0.06 | 0.018 | 108.0 |

TABLE I-continued

In Vitro Topoisomerase I Activity and Cytotoxicity of Topoisomerase-I Selective Analogs against Murine P388 Leukemia Cells.

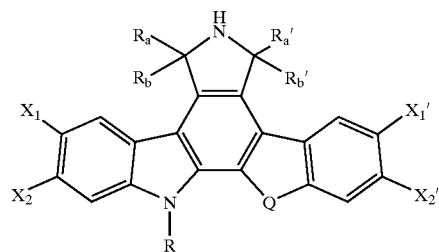

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I[§] EC$_{50}$ ($\mu$M) | P388[†] IC$_{50}$ ($\mu$M) | Selectivity Index R/S[‡] |
|---|---|---|---|---|---|---|---|---|---|
| 3 | F | F | H | H | S |  | 0.06 | 0.016 | 110.4 |
| 4 | F | F | H | H | NH |  | 0.22 | 0.012 | 110.9 |
| 5 | F | F | F | F | NH |  | ND | 0.032 | 112.5 |
| 6 | F | F | H | H | S |  | 0.07 | 0.068 | >116.3 |

TABLE I-continued

In Vitro Topoisomerase I Activity and Cytotoxicity of Topoisomerase-I Selective Analogs against Murine P388 Leukemia Cells.

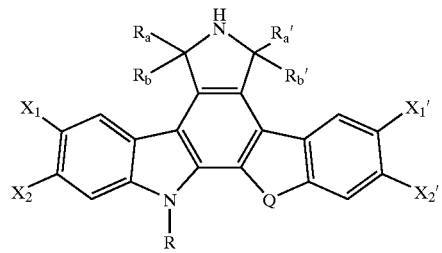

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I$^\S$ EC$_{50}$ ($\mu$M) | P388$^\dagger$ IC$_{50}$ ($\mu$M) | Selectivity Index R/S$^\ddagger$ |
|---|---|---|---|---|---|---|---|---|---|
| 7 | F | F | H | H | NH | (sugar with Me-S(=O)-CH2, OH, OH, OH) | 0.01 | 0.076 | >116.4 |
| 8 | F | F | F | F | S | (sugar with F-CH2, OH, OH, OH) | 0.12 | 0.052 | 119.1 |
| 9 | F | F | F | F | S | (sugar with F-CH2, OH, OH) | 0.23 | 0.035 | 120.2 |
| 10 | F | F | H | H | NH | (sugar with HO-CH2, OH, OH, N3) | 0.02 | 0.068 | 121.3 |

TABLE I-continued

In Vitro Topoisomerase I Activity and Cytotoxicity of Topoisomerase-I Selective Analogs against Murine P388 Leukemia Cells.

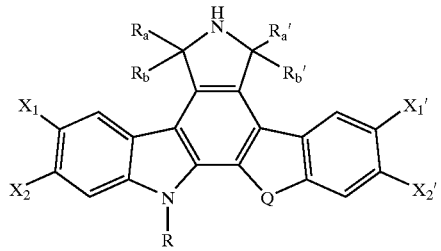

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I$^§$ EC$_{50}$ ($\mu$M) | P388$^†$ IC$_{50}$ ($\mu$M) | Selectivity Index R/S$^‡$ |
|---|---|---|---|---|---|---|---|---|---|
| 11 | F | F | H | H | NH | (sugar) | ND | 0.016 | 125.3 |
| 12 | F | F | F | F | S | (sugar) | 0.02 | 0.002 | 131.5 |
| 13 | F | F | H | H | S | (sugar) | 0.16 | 0.10 | 140.0 |
| 14 | F | F | F | F | NH | (sugar) | 0.03 | 0.006 | 140.3 |
| 15 | F | F | H | H | NH | (sugar) | 0.03 | 0.005 | >149.7 |

TABLE I-continued

In Vitro Topoisomerase I Activity and Cytotoxicity of Topoisomerase-I Selective Analogs against Murine P388 Leukemia Cells.

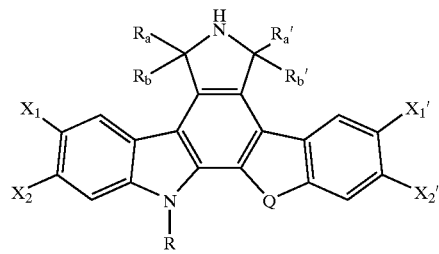

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I[§] EC$_{50}$ ($\mu$M) | P388[†] IC$_{50}$ ($\mu$M) | Selectivity Index R/S[‡] |
|---|---|---|---|---|---|---|---|---|---|
| 16 | F | Br | H | H | O | | 0.05 | 0.047 | 177.4 |
| 17 | F | F | F | F | NH | | 0.45 | 0.041 | 179.2 |
| 18 | F | F | F | F | NH | | ND | 0.008 | 184.8 |
| 19 | F | F | H | H | NH | | 0.06 | <0.003 | >195.2 |
| 20 | F | F | H | H | NH | | 0.02 | 0.002 | 201.2 |

TABLE I-continued

In Vitro Topoisomerase I Activity and Cytotoxicity of Topoisomerase-I Selective Analogs against Murine P388 Leukemia Cells.

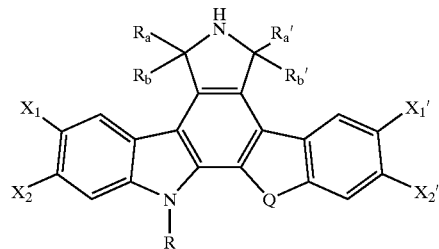

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I[§] $EC_{50}$ (µM) | P388[†] $IC_{50}$ (µM) | Selectivity Index R/S[‡] |
|---|---|---|---|---|---|---|---|---|---|
| 21 | F | F | F | F | NH | (sugar) | 0.07 | 0.005 | 207.7 |
| 22 | F | F | F | F | NH | (sugar) | 0.08 | 0.014 | 287.7 |
| 23 | F | F | H | H | S | (sugar) | ND | 0.025 | 306.8 |
| 24 | F | F | H | H | NH | (sugar) | 0.02 | 0.002 | 379.0 |

TABLE I-continued

In Vitro Topoisomerase I Activity and Cytotoxicity of Topoisomerase-I
Selective Analogs against Murine P388 Leukemia Cells.

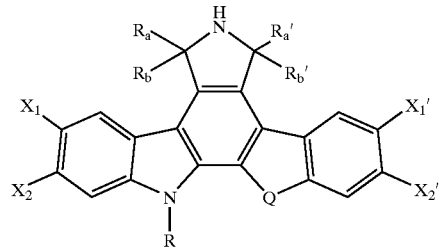

(Note: The structure immediately above is to be used to define the examples below.
For all examples, except 32 and 34, $R_a$ and $R_b$ are taken together as O; and $R_a'$ and $R_b'$
are taken together as O. For example 32, both $R_a$ and $R_b$ are H and $R_a'$ and $R_b'$ are
taken together as O. For example 34, $R_a$ and $R_b$ are taken together as O; and both $R_a'$
and $R_b'$ are H.)

| Ex. | $X_1$ | $X_1'$ | $X_2$ | $X_2'$ | Q | R | Topo I[§] EC$_{50}$ (μM) | P388[†] IC$_{50}$ (μM) | Selectivity Index R/S[‡] |
|---|---|---|---|---|---|---|---|---|---|
| 25 | F | F | H | H | NH | (sugar: O, HO-CH2, OH, OH, F, F) | 0.01 | 0.003 | 381.5 |
| 26 | F | F | F | F | S | (sugar: O, F-CH2, OH, OH, F) | 0.13 | 0.011 | 387.8 |
| 27 | F | F | H | H | NH | (sugar: O, F-CH2, OH, OH, F) | 0.15 | 0.004 | 448.4 |
| 28 | F | F | F | F | NH | (sugar: O, HO-CH2, OH, OH, F) | 0.05 | 0.004 | 499.2 |

TABLE I-continued

In Vitro Topoisomerase I Activity and Cytotoxicity of Topoisomerase-I Selective Analogs against Murine P388 Leukemia Cells.

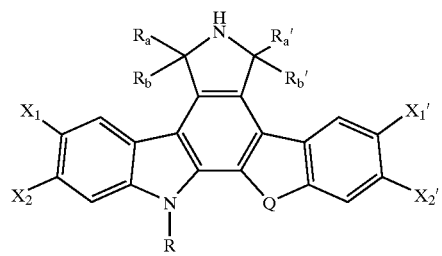

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I[§] EC$_{50}$ (μM) | P388[†] IC$_{50}$ (μM) | Selectivity Index R/S[‡] |
|---|---|---|---|---|---|---|---|---|---|
| 29 | F | F | F | F | NH | 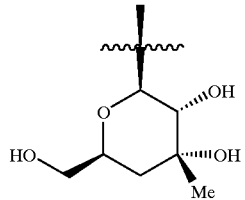 | ND | 0.005 | 539.6 |
| 30 | F | F | F | F | S | 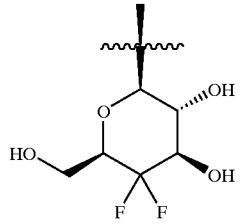 | 0.01 | 0.000 | 575.5 |
| 31 | F | F | H | H | NH | 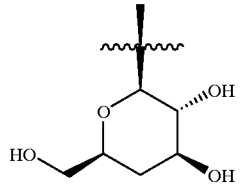 | 0.08 | 0.004 | 720.7 |

TABLE I-continued

In Vitro Topoisomerase I Activity and Cytotoxicity of Topoisomerase-I Selective Analogs against Murine P388 Leukemia Cells.

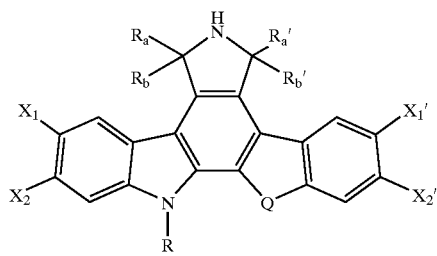

(Note: The structure immediately above is to be used to define the examples below. For all examples, except 32 and 34, $R_a$ and $R_b$ are taken together as O; and $R_a'$ and $R_b'$ are taken together as O. For example 32, both $R_a$ and $R_b$ are H and $R_a'$ and $R_b'$ are taken together as O. For example 34, $R_a$ and $R_b$ are taken together as O; and both $R_a'$ and $R_b'$ are H.)

| Ex. | $X_1$ | $X_1'$ | $X_2$ | $X_2'$ | Q | R | Topo I[§] EC$_{50}$ ($\mu$M) | P388[†] IC$_{50}$ ($\mu$M) | Selectivity Index R/S[‡] |
|---|---|---|---|---|---|---|---|---|---|
| 32 | F | F | H | H | NH | 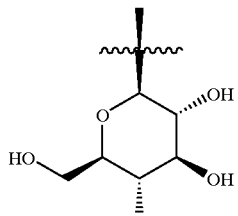 | ND | 0.005 | 1051.8 |
| 33 | F | F | F | F | S | 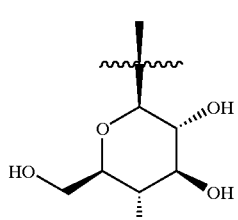 | 0.05 | <0.003 | >1657.6 |
| 34 | F | F | H | H | NH | 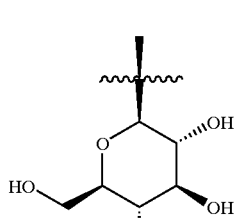 | ND | 0.002 | 2859.5 |

[§]The topoisomerase-I assay mentioned above was used as the screening assay. Median effect concentration of analog for inducing single-strand breaks in the DNA substrate.

[†]Median cytotoxic concentration (IC$_{50}$) following 3 days of continuous exposure of analog to P388 murine leukemia cells or P388/CPT45 cells that have acquired high levels of camptothecin resistance.

[‡]Ratio resulting from the IC$_{50}$ value obtained for P388/CPT45 cells divided by that obtained for parental P388 cells.

TABLE II

In Vitro Topoisomerase I Activity and Cytotoxicity of Topoisomerase I Non-Selective Analogs against Murine P388 Leukemia Cells.

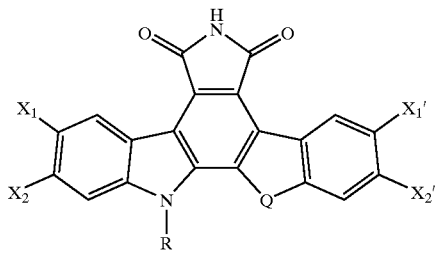

(Note: The structure immediately above is to be used to define the examples below.)

| Ex. | $X_1$ | $X_1'$ | $X_2$ | $X_2'$ | Q | R | Topo I[§] EC$_{50}$ ($\mu$M) | P388[\\] IC$_{50}$ ($\mu$M) | Selectivity Index R/S[‡] |
|---|---|---|---|---|---|---|---|---|---|
| 35 | F | F | H | H | S | (2-thio-4-hydroxypyrimidine sugar) | 0.24 | >7.68 | <1.0 |
| 36 | F | H | H | H | S | (aminomethyl sugar) | 0.18 | 8.99 | <1.1 |
| 37 | H | H | F | F | NH | (hydroxymethyl sugar) | 0.24 | 0.26 | 8.7 |
| 38 | F | F | H | H | S | (ornithine-amide sugar) | ND | 1.115 | 2.5 |

TABLE II-continued

In Vitro Topoisomerase I Activity and Cytotoxicity of Topoisomerase I Non-Selective Analogs against Murine P388 Leukemia Cells.

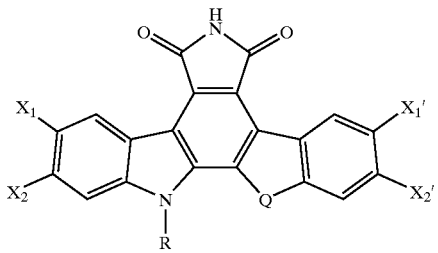

(Note: The structure immediately above is to be used to define the examples below.)

| Ex. | $X_1$ | $X_1'$ | $X_2$ | $X_2'$ | Q | R | Topo I[§] EC$_{50}$ ($\mu$M) | P388[†] IC$_{50}$ ($\mu$M) | Selectivity Index R/S[‡] |
|---|---|---|---|---|---|---|---|---|---|
| 39 | F | F | H | H | NH | (2-deoxy-6-fluoro sugar) | 0.10 | 0.235 | 5.0 |
| 40 | F | F | H | H | O | (6-amino sugar) | 0.03 | 1.78 | 5.5 |
| 41 | F | F | H | H | NH | (2-deoxy-6-amino sugar) | 0.02 | 0.072 | 27.3 |
| 42 | H | H | F | F | NH | (3-keto sugar) | 0.28 | 0.127 | 29.3 |

[§]The topoisomerase-I assay mentioned above was used as the screening assay. Median effect concentration of analog for inducing single-strand breaks in the DNA substrate.
Note: Topo I activity was unpredictable.
[†]Median cytotoxic concentration (IC$_{50}$) following 3 days of continuous exposure of analog to P388 murine leukemia cells or P388/CPT45 cells that have acquired high levels of camptothecin resistance.
[‡]Ratio resulting from the IC$_{50}$ value obtained for P388/CPT45 cells divided by that obtained for parental P388 cells.

In Vivo Antitumor Activity
Materials and Methods

Compounds: Examples of this invention were administered in an appropriate vehicle such as cremophor/ethanol/water (10%/10%/80%), in normal saline, water/carboxymethylcellulose vehicle.

All compounds were tested at several dose levels, with attempts each time to achieve their maximum tolerated dose (MTD). A MTD was defined as the highest dose tested which did not cause more than one death per set of 8 mice. The optimal dose (OD) was the dose producing the best therapeutic effect, and was usually, but not always, synonymous with the MTD.

Tumors: Human tumors (HCT-116 and HT-29 colon carcinomas) were grown as xenografts in Balb/c athymic (nude) female mice.

Antitumor assays. All tumors were implanted subcutaneously (sc) as 3–4mm fragments using a 13 gauge trochar. There were generally eight mice per treatment and control group. When treatment was delayed until tumors had obtained a certain size (weight), referred to as a staged tumor experiment (expt.), tumor-bearing mice were selected so that their tumors fell within a limited range of sizes for the particular expt.

Tumors were measured by calipers, and tumor weight calculated by the formula length (mm) times (x) width $(mm)^2/2$=tumor weight (mg). The median time (in days) to reach a predetermined tumor target size (for example, 500 mg) for untreated, control (C) mice relative to the time to reach the same target size for treated (T) mice, was calculated as a T-C value. T-C values were divided by the tumor volume doubling time (TVDT), and multiplied by 3.32, to yield a gross log cell kill (LCK) value, [i.e., (T-C)/TVDT× 3.32=LCK].

A mouse was considered cured if there was no palpable tumor after a period of time equal to 10×TVDT post-reatment (Rx).

Table III shows representative examples, but is not limited to those, which were evaluated in this paradigm.

TABLE III

In Vivo Activity of Topoisomerase I Selective Analogs against Human Colon Carcinoma Cells.

| | HT29 | | | HT116 | | |
|---|---|---|---|---|---|---|
| | LCK[†] | | MTD[‡] | LCK[†] | | MTD[‡] |
| Example | Analog | CPT-11 | (mpkpi) | Analog | CPT-11 | (mpkpi) |
| 9 | >1.4 | 1.4 | >22 | >3.4 | >3.4 | >22 |
| 24 | 2.1 | 1.1 | 15 | 1.3 | 1.4 | 10 |
| 26 | 1.4 | 2.1 | >9 | >3.4 | >3.4 | >9 |
| 27 | 1.9[a] | 0.8 | 11 | >1.4[c] | 1.4 | 8 |
| 30 | >1.4 | 1.4 | 16 | — | — | — |
| 33 | >2.3[b] | 0.8 | 11 | 2.3 | 2.0 | 10 |

[a]= 1 out of 8 are cures
[b]= 2 out of 8 are cures
[c]= possible cures
[†]Log Cell Kill (LCK) is equivalent to (T-C)/(TVDT × 3.32).
[‡]Optimal or maximum tolerated dose level tested in milligrams per kilogram.

The compounds which constitute this invention and their methods of preparation will appear more fully from a consideration of the following examples which are given for the purpose of illustration only and are not to be construed as in any way limiting the scope of the invention.

Synthesis of Intermediates

Several intermediate compounds as well as other conventional starting materials, used in the preparation of final products of Formula I, were generally known in the literature or were commercially available. Additional Examples of formula I compounds, which may be synthesized by modifications of the foregoing synthetic procedures mentioned in WO 98/07433 and co-pending U.S. application, Ser. No. 08/914566 (both herein incorporated by reference), are set forth here wherein the substituents are as depicted in formula I, unless otherwise mentioned. Representative syntheses of some of these compounds are nevertheless provided herein below.

All anhydrous reactions were performed under an atmosphere of nitrogen or argon using either commercially available dry solvents or freshly distilled solvents. Melting points were determined in an open capillary tube with a Thomas-Hoover melting point apparatus and are uncorrected. Column chromatography was performed using EM Science silica gel 60 (230–400 mesh) with the designated solvent system as eluant. Thin-layer chromatography was done on E. Merck silica gel 60 $F_{254}$ plates (0.5 mm). HPLC purity determinations were done using either a Shimadzu LC-10AS with a SPD-10AV UV-Vis detector and one of the following columns; YMC Combiscreen ODS-A (4.6×50 mm), or HP Zorbax SB-C18 (4.6×750 mm); or, an HP 1090 DR5 with a diode array detector and a Waters Nova-Pak C18 column (3.9×150 mm). Infrared spectra were recorded on a Nicolet Protégé 460 FTIR as thin films or KBr pellets. $^1$HNMR spectra were recorded on either a Bruker AMX-400 or a Bruker ARX-500 NMR spectrometer and chemical shifts are expressed in parts per million (ppm or δ) with the solvent in use as internal standard. Coupling constants are given in hertz (Hz) and multiplets are designated as follows; singlet (s), doublet (d), triplet (t), quartet (q), muliplet (m), and broad (br). Low resolution mass spectra were determined on a Finnigan Matt TSQ-7000 triple stage quadrapole spectrometer (positive/negative ESI) operated in the negative ion mode. High resolution mass spectra were determined using a Kratos MS50 EBE mass spectrometer using high resolution peak matching in the negative ion mode.

All compounds exhibited satisfactory IR, MS, $^1$H and $^{13}$C NMR, elemental analysis and/or high resolution mass spectra where available.

EXAMPLE 4

12-[6-Deoxy-6-fluoro-β-D-galactopyranosyl]-3,9-difluoro-12,13-dihydro-5H-indolo[2,3-a]pyrrolo[3,4-c]carbazole-5,7(6H)-dione

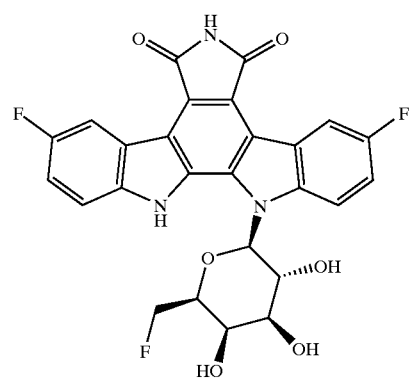

LRMS (neg. ESI, M-H⁻) for $C_{26}H_{18}F_3N_3O_6$ m/z 524.

EXAMPLE 5

12-[4,6-Dideoxy-6-fluoro-2-O-leucyl-β-D-glucopyranosyl]-2,3,9,10-tetrafluoro-12,13-dihydro-5H-indolo[2,3-a]pyrrolo[3,4-c]carbazole-5,7(6H)-dione

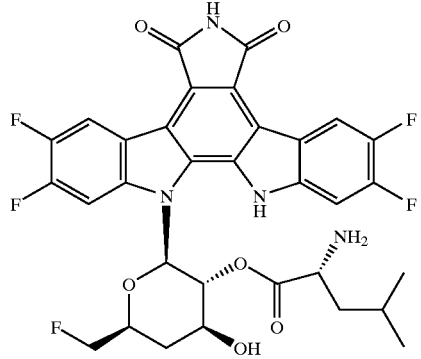

To a solution of 12-[4,6-dideoxy-6-fluoro-β-D-glucopyranosyl]-2,3,9,10-tetrafluoro-12,13-dihydro-5H-indolo[2,3-a]pyrrolo[3,4-c]carbazole-5,7(6H)-dione (0.100 g, 0.18 mmol) in 5 mL of THF was added a solution of Z-Leu-OH (0.057 g, 0.216 mmol) in 1 mL of THF, followed by DMAP (0.026 g, 0.216 mmol) and DCC (0.045 g, 0.216 mmol). The resulting mixture was stirred at room temperature for 18 h and then it was diluted with ethyl acetate, washed (cold 1N HCl, H$_2$O, brine), dried (MgSO$_4$) and evaporated. Flash chromatography (SiO$_2$/2–30% ethyl acetate-hexane) of the residue afforded the protected leucyl ester (0.112 g, 70%) as a yellow solid which was used directly in the next step.

To the protected leucyl ester (0.300 g, 0.38 mmol) and 20% Pd(OH)$_2$/C (0.3 g) in 30 mL of dry THF was added 4M HCl in dioxane (0.45 mL, 1.8 mmol) and the resulting mixture was hydrogenated (1 atm) for 16 h. The mixture was then filtered (Millipore, 0.22 μm) and the filtrate was evaporated to give the essentially pure title compound (0.243 g, 92%) as its hydrochloride;

LRMS (neg. ESI, M–H$^-$) for C$_{32}$H$_{27}$F$_5$N$_4$O$_6$ m/z 657.

EXAMPLE 8

13-[6-Dideoxy-6-fluoro-β-D-glucopyranosyl]-2,3,9,10-tetrafluoro-5H,13H-benzo[b]thienyl[2,3-a]pyrrolo[3,4-c]carbazole-5,7(6H)-dione

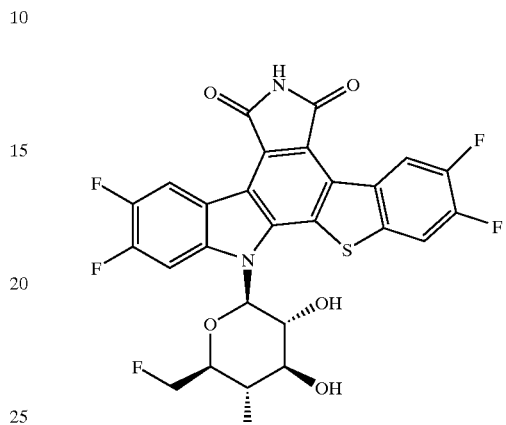

LRMS (neg. ESI, M–H$^-$) for C$_{26}$H$_{15}$F$_5$N$_2$O$_6$S m/z 577; HRMS (pos. ESI, M+H$^+$) calcd for C$_{26}$H$_{15}$F$_5$N$_2$O$_6$S m/z 579.064780; found 579.06476.

EXAMPLE 9

12-[4,6-Dideoxy-6-fluoro-β-D-glucopyranosyl]-2,3,9,10-tetrafluoro-5H,13H-benzo[b]thienyl[2,3-a]pyrrolo[3,4-c]carbazole-5,7(6H)-dione

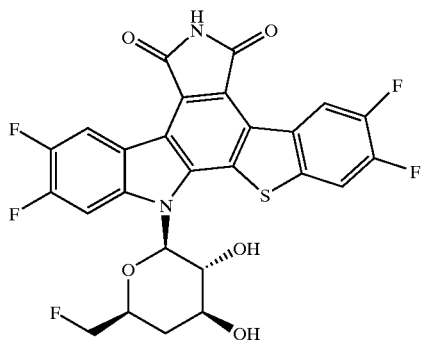

LRMS (neg. ESI, M–H$^-$) for C$_{26}$H$_{15}$F$_5$N$_2$O$_5$S m/z 561.

EXAMPLE 11

12-[4,6-Dideoxy-β-D-glucopyranosyl]-3,9-difluoro-12,13-dihydro-5H-indolo[2,3-a]pyrrolo[3,4-c]carbazole-5,7(6H)-dione

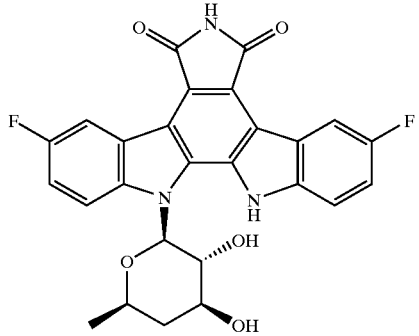

A mixture of 3,9-difluoro-12-(2,3-di-O-benzyl-4-deoxy-β-D-glucopyranosyl)-6,7,12,13-tetrahydro-(5H)indolo[2,3-a]pyrrolo[3,4-c]carbazole-5,7-dione (0.312 g, 0.45 mmol) and freshly activated, pulverized 4A molecular sieves (0.5 g) in 15 mL of dichloromethane was cooled at 5° C. under Ar and then triethylamine (0.095 mL, 0.68 mmol) and methanesulfonyl chloride (0.039 mL, 0.50 mmol) were added sequentially. The mixture was stirred at the same temperature for 3 h and then the mixture was quenched with 10% saturated aqueous NaHCO$_3$, diluted with ethyl acetate and then filtered. The filtrate was washed (H$_2$O, brine), dried (Na$_2$SO$_4$) and evaporated to give a yellow glass. This material was taken up in 15 mL of acetone, NaI (0.675 g, 4.50 mmol) was added and the mixture was heated to reflux under Ar for 17 h. The cooled mixture was then evaporated to dryness and the residue was taken up in ethyl acetate, washed (H$_2$O, brine) dried (Na$_2$SO$_4$) and evaporated. The resulting solid was chromatographed (SiO$_2$/ethyl acetate-hexane, 1:1) to give 3,9-difluoro-12-(2,3-di-O-benzyl-4,6-dideoxy-6-iodo-β-D-glucopyranosyl)-6,7,12,13-tetrahydro (5H)indolo[2,3-a]pyrrolo[3,4-c]carbazole-5,7-dione (0.276 g, 77% overall) as a yellow glass. To an ice-cold solution of this iodide in 10 mL of dry THF was added DBU (0.157 mL, 1.05 mmol) and the solution was then kept at room temperature for 5 days. The resulting mixture was quenched with saturated aqueous NH$_4$Cl, diluted with ethyl acetate and then washed (H$_2$O, brine), dried (Na$_2$SO$_4$) and evaporated to give the product (0.232 g, 99%) as a yellow glass. To a solution of this material in dry THF was added 20% Pd(OH)$_2$/C and the mixture was hydrogenated (balloon pressure) until the reaction was complete by tlc. The mixture was then filtered (Celite) and the flitrate evaporated to give a yellow glass. Column chromatography (Sephadex LH-20/methanol) afforded the pure title compound as a yellow solid:

LRMS (neg. ESI, M–H$^-$) for C$_{26}$H$_{19}$F$_2$N$_3$O$_5$ m/Z 490.

EXAMPLE 12

12-[6-Amino-4,6-dideoxy-4-fluoro-β-D-glucopyranosyl]-2,3,9,10-tetrafluoro-5H,13H-benzo[b]thienyl[2,3-a]pyrrolo[3,4-c]carbazole-5,7(6H)-dione

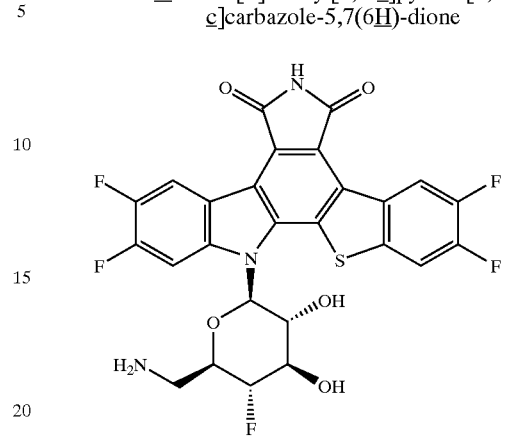

12-(4-Deoxy-4-fluoro-β-D-glucopyranosyl)-2,3,9,10-tetrafluoro-5H,13H-benzo[b]thienyl[2,3-a]pyrrolo[3,4-c]carbazole-5,7(6H)-dione (0.20 g, 0.35 mmol) was dissolved in dry pyridine (10 mL) under nitrogen at room temperature and treated to flame-dried, powdered 4Å molecular sieves (3.0 g). After the mixture was cooled to –30° C. for 15 min, methanesulfonyl chloride (0.030 mL, 0.38 mmol,) was added neat. The mixture was stirred at –30° C. for 15 min and then it was allowed to warm to 0° C. over 15 min, and finally it was quenched with ethyl acetate and ethanol. The resulting mixture was filtered (Celite) and and the filtrate concentrated in vacuo. The residue was taken up in ethyl acetate and tetrahydrofuran, washed (0.1 N HCl, saturated sodium bicarbonate, brine), dried and evaporated. This afforded 12-[4-deoxy-4-fluoro-6-O-(methanesulfonyl)-β-D-glucopyranosyl]-5H,13H-benzo[b]thienyl[2,3-a]pyrrolo[3,4-c]carbazole-5,7(6H)-dione as a yellow solid which was sufficiently pure to be used directly in the next step;

$^1$H NMR (500 MHz, DMSO-d$_6$) δ 11.61 (br s, 1H), 9.76–9.66 (2m, 1H), 9.01–8.94 (2m, 1H), 8.22–8.19 (2m, 1H), 8.12–8.00 (2m, 1H), 7.58–7.48 (2m, 2H)6.33 and 6.6.23 (2d, J=8.8, 9.1 Hz, 1H), 5.72–5.15 (series of m, 3H), 4.66–4.53 (m, 2H), 4.07–3.98 (m, 2H), 3.62–3.56 (m, 2H), 3.13 and 3.10 (2s, 3H); MS (–ESI, M–H$^-$) m/z 655.

To a stirred solution of 12-[4-deoxy-4-fluoro-6-O-(methanesulfonyl)-β-D-glucopyranosyl]-5H,13H-benzo[b]thienyl[2,3-a]pyrrolo[3,4-c]carbazole-5,7(6H)-dione (0.230 g, 0.351 mmol) in anhydrous dimethylformamide (90 mL) was added sodium azide (0.228 g, 3.51 mmol) and the mixture was heated to 140° C. for 4 h. After cooling to ambient temperature the mixture was diluted with tetrahydrofuran-ethyl acetate and water. The organic phase was separated, washed (saturated sodium bicarbonate solution, brine), dried and evaporated. The aqueous phase was back-extracted with ethyl acetate (×3) and the organic extract was treated as before. Flash chromatography of the residue (SiO$_2$/10% methanol in chloroform) yielded 12-[(6-azido-4,6-dideoxy-4-fluoro-β-D-glucopyranosyl)-2,3,9,10-tetrafluoro-5H,13H-benzo[b]thienyl[2,3-a]pyrrolo[3,4-c]carbazole-5,7(6H)-dione as a yellow solid;

$^1$H NMR (500 MHz, DMSO-d$_6$) d 11.60 (br s, 1H), 9.76–9.60 (2m, 1H), 9.09–8.98 (2m, 1H), 8.18–8.15 (3m,

1H), 8.01–7.91 (m, 1H), 6.28 and 6.20 (2d, J=8.9 and 9.4 Hz, 1H), 5.64–5.14 (m, 1H), 5.06–4.76 (series of m, 1H), 4.35–3.95 (series of m, 3H 3.86–3.31 (m, 3H); MS (–ESI, M–H⁻) m/z 602.

A mixture of 12-[(6-azido-4,6-dideoxy-4-fluoro-β-D-glucopyranosyl)-2,3,9,10-tetrafluoro-5H,13 H-benzo[b]thienyl[2,3-a]pyrrolo[3,4-c]carbazole-5,7(6 H)-dione (0.100 g, 0.166 mmol) and triphenylphosphine (0.130 g, 0.497 mmol) in a mixture of tetrahydrofuran (15 mL) and water (2 mL) was heated to 50° C. under $N_2$ for 16 h. The cooled mixture was then treated with concentrated ammonium hydroxide solution (10 mL) for 1 h at 50° C. Upon cooling to room temperature, the mixture was diluted with tetrahydrofuran and preadsorbed onto silica gel. Purification of the residue by flash chromatography ($SiO_2$/dichloromethane-tetrahydrofuran-methanol, 7:2.5:0.5 then 6:2:2) gave the title compound as a yellow solid. This material was taken up in THF, methanolic HCl was added and the mixture was evaporated to give the hydrochloride (0.015 g, 16%) as a granular, yellow solid;

¹H NMR (500 MHz, DMSO-$d_6$) δ 11.66 (br s, 1H), 9.86–9.82 (2m, 1H), 9.11–9.06 (2m, 1H), 8.49–8.46 (m, 1H),8.29–8.25 (m, 1H), 8.19 (br s, 3H), 6.32 and 6.1277 (2d, J=8.9, 9.4 Hz, 1H), 5.74–5.70 (2m, 1H), 5.22–5.10 (3m, 2H), 4.40–4.01 (series of m, 7H); LRMS (neg. ESI, M–H⁻) for $C_{26}H_{16}F_5N_3O_5S$ m/z 576.

EXAMPLE 17

12-[3,6-Difluoro-3,4,6-trideoxy-β-D-allopyranosyl]-2,3,9,10-tetrafluoro-12,13-dihydro-5H-indolo[2,3-a]pyrrolo[3,4-c]carbazole-5,7(6H)-dione.

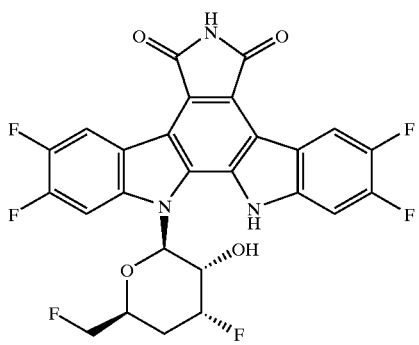

LRMS (neg. ESI, M–H⁻) for $C_{26}H_{15}F_6N_3O_4$ m/z 546.

EXAMPLE 18 and 29

12-[4-Deoxy-3-methyl-β-D-glucopyranosyl]-2,3,9,10-tetrafluoro-12,13-dihydro-5H-indolo[2,3-a]pyrrolo[3,4-c]carbazole-5,7(6H)-dione (Ib: $X_1$=$X_1'$=$X_2$=$X_2'$=F; $R_6$=H; $R_2$=$R_5$=OH; $R_3$=OH, $CH_3$, $R_4$=$H_2$; Q=NH) and 12-[4-Deoxy-3-methyl-β-D-allopyranosyl]-2,3,9,10-tetrafluoro-12,13-dihydro-5H-indolo[2,3-a]pyrrolo[3,4-c]carbazole-5,7(6H)-dione

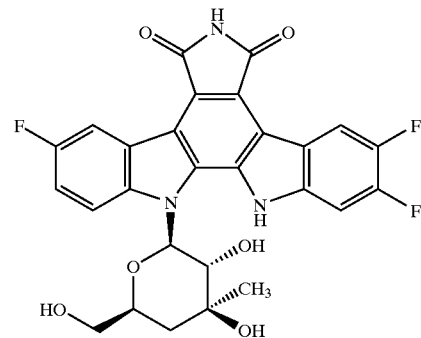

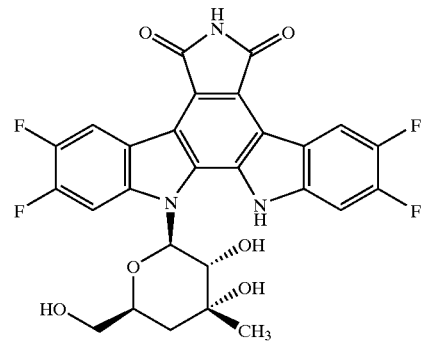

To a solution of 12-[4-deoxy-2,3,6-tri-O-benzyl-β-D-glucopyranosyl]-2,3,9,10-tetrafluoro-12,13-dihydro-5 H-indolo[2,3-a]pyrrolo[3,4-c]carbazole-5,7(6H)-dione (6.49 g, 7.97 mmol) in 90 mL of acetic anhydride was added solid $I_2$ (0.406 g, 1.6 mmol) and the mixture was stirred at room temperature for 16 h. The resulting mixture was diluted with ethyl acetate, washed (30% aq. $Na_2S_2O_3$, saturated aq. $NaHCO_3$, $H_2O$, brine) dried ($MgSO_4$) and evaporated. The residue was taken up in methanol (150 mL), 15 mL of concentrated $NH_4OH$ was added and the mixture was stirred at room temperature for 18 h. The mixture was then evaporated to dryness and the residue was chromatographed ($SiO_2$/hexane-ethyl acetate, 95:5 to 1:1) to give 12-[4-deoxy-2,3,-di-O-benzyl-β-D-glucopyranosyl]-2,3,9,10-tetrafluoro-12,13-dihydro-5H-indolo[2,3-a]pyrrolo[3,4-c]carbazole-5,7(6H)-dione (2.35 g, 41%) and then 12-[4 deoxy-2-O-benzyl-β-D-glucopyranosyl]-2,3,9,10-tetrafluoro-12,13-dihydro-5H-indolo[2,3-a]pyrrolo[3,4-c]carbazole-5,7(6H)-dione (2.40 g, 48%), both as yellow solids.

To a solution of 12-[4-deoxy-2-O-benzyl-β-D-glucopyranosyl]-2,3,9,10-tetrafluoro-12,13-dihydro-5 H-indolo-[2,3-a]pyrrolo[3,4-c]carbazole-5,7(6H)-dione (0.500 g, 0.79 mmol) in 6 mL of dry DMF, at 5° C. under Ar, was added tert-butyldiphenylsilyl chloride (0.205 mL, 0.79 mmol) and imidazole (0.161 g, 2.37 mmol). After stirring this mixture at room temperature for 20 h it was re-cooled at 5° C. and more tert-butyldiphenylsilyl chloride (0.205 mL, 0.79 mmol) and imidazole (0.161 g, 2.37 mmol) were added. The resulting mixture was stirred at room temperature for 2.5 h and then it was diluted with ethyl acetate, washed (1M NaHCO$_3$, brine), dried (MgSO$_4$) and evaporated. Chromatography (SiO$_2$/20–35% ethyl acetate-hexane) of the residue afforded 12-[4-deoxy-6-O-(tert-butyldiphenylsilyl)-2-O-benzyl-β-D-glucopyranosyl]-2,3,9,10-tetrafluoro-12,13-dihydro-5H-indolo[2,3-a]pyrrolo[3,4-c]carbazole-5,7(6H)-dione (0.474 g, 69%); MS (ESI$^-$) m/e 870 (M–H)$^-$. To a solution of a portion (0.050 g, 0.057 mmol) of this material in 2 mL of dichloromethane was added a suspension of Dess-Martin periodinane (0.048 g, 0.114 mmol) in 3 mL of dichloromethane and the mixture was stirred for 30 min. The mixture was then diluted with ethyl acetate, washed (cold 30% aq. Na$_2$S$_2$O$_3$,1M NaHCO$_3$, H$_2$O, brine), dried (MgSO$_4$) and evaporated. Prep tlc (SiO$_2$/ ethyl acetate-hexane, 2:3) of the residue afforded 12-[4-deoxy-6-O-(tert-butyldiphenylsilyl)-2-O-benzyl-3-oxo-β-D-glucopyranosyl]-2,3,9,10-tetrafluoro-12,13-dihydro-5H-indolo[2,3-a]pyrrolo[3,4-c]carbazole-5,7(6H)-dione (0.035 g, 70%) as a gum which solidified on standing; MS (ESI$^-$) m/e 868 (M–H)$^-$.

To a solution of this material ( ) in 5 mL of dry THF, at –78° C. under Ar, was added MeMgBr (1.4M solution in THF-toluene, 0.49 mL, 0.69 mmol) dropwise. The resulting mixture was stirred at –78 C. for 2 h and then it was allowed to warm to –20° C. over 2 h. The mixture was then quenched with 1 mL of 1 M NaHCO$_3$, and then it was patitioned with ethyl acetate (20 mL) and 1 M NaHCO$_3$ (5 mL). The organic phase was separated, washed (H$_2$O brine), dried (MgSO$_4$) and evaporated. Flash chromatography (SiO$_2$/2–28% ethyl acetate-hexane) of the residue afforded 12-[4-deoxy -6-O-(tert-butyldiphenylsilyl)-2-O-benzyl-3-methyl-β-D-allopyranosyl]-2,3,9,10-tetrafluoro-12,13-dihydro-5H-indolo[2,3-a]pyrrolo[3,4-c]carbazole-5,7(6H)-dione (0.052 g, 43%) and then 12-[4-deoxy-6-O-(tert-butyldiphenylsilyl)-2-O-benzyl-3-methyl-β-D-glucopyranosyl]-2,3,9,10-tetrafluoro-12,13-dihydro-5H-indolo[2,3-a]pyrrolo[3,4-c]carbazole-5,7(6H)-dione (0.028 g, 23%); MS (ESI$^-$) m/e 884 (M–H)$^-$. To a cold (5° C.) solution of 12-[4-deoxy-6-O-(tert-butyldiphenylsilyl)-2-O-benzyl-3-methyl -β-D-allopyranosyl]-2,3,9,10-tetrafluoro-12,13-dihydro-5H-indolo[2,3-a]pyrrolo [3,4-c]carbazole-5,7(6H)-dione (0.050 g, 0.056 mmol) in 5 mL of MeCN under Ar was added Et$_3$N.3HF (0.091 mL, 0.56 mmol) and the mixture was stirred at room temperature for 2 days. The resulting mixture was diluted with ethyl acetate, washed (1M NaHCO$_3$, H$_2$O, brine) dried (MgSO$_4$) and evaporated. The residue was purified by prep tlc (SiO$_2$/ethyl acetate-hexane, 3:2) to give 12-[4-deoxy-2-O-benzyl-3-methyl-β-D-allopyranosyl]-2,3,9,10-tetrafluoro-12,13-dihydro-5H-indolo[2,3-a]pyrrolo[3,4-c]carbazole-5,7(6H)-dione (0.026 g, 72%) as a yellow solid; MS (ESI$^-$) m/e 646 (M–H)$^-$.

A mixture of this material (0.025 g, 0.039 mmol) and 20% Pd(OH)$_2$/C (0.025 g) in 6 mL of chloroform-methanol (1:1) was hydrogenated (1 atm) for 18 h and then it was filterwed and the filter-cake was washed with THF. Evaporation of the filtrate and purification of the residue by prep tlc (SiO$_2$/ THF-hexane, 1:1) afforded 12-[4-deoxy-3-methyl-β-D-allopyranosyl]-2,3,9,10-tetrafluoro-12,13-dihydro-5H-indolo[2,3-a]pyrrolo[3,4-c]carbazole-5,7(6H)-dione (0.010 g, 45%) as a yellow solid;

LRMS (neg. ESI, M–H$^-$) for C$_{27}$H$_{19}$F$_4$N$_3$O$_6$ m/z 556.

Deprotection of 12-[4-deoxy-6-O-(tert-butyldiphenylsilyl)-2-O-benzyl-3-methyl -β-D-glucopyranosyl]-2,3,9,10-tetrafluoro-12,13-dihydro-5H-indolo[2,3-a]pyrrolo[3,4-c]carbazole-5,7(6H)-dione in similar fashion afforded 12-[4-deoxy-3-methyl-β-D-glucopyranosyl]-2,3,9,10-tetrafluoro-12,13-dihydro-5H-indolo[2,3-a]pyrrolo[3,4-c]carbazole-5,7(6H)-dione as a yellow solid in 57% overall yield; LRMS (neg. ESI, M–H$^-$) for C$_{27}$H$_{19}$F$_4$N$_3$O$_6$ m/z 556.

EXAMPLE 20

12-[4-Deoxy-β-D-allopyranosyl)-3,9-difluoro-12,13-dihydro-5H-indolo [2,3-a]pyrrolo[3,4-c]carbazole-5,7(6H)-dione

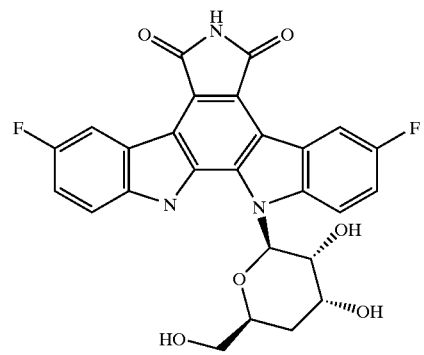

LRMS (neg. ESI, M–H$^-$) for C$_{26}$H$_{19}$F$_2$N$_3$O$_6$ m/z 506.

EXAMPLE 22

12-[4,6-Difluoro-4,6-dideoxy-β-D-glucopyranosyl]-2,3,9,10-tetrafluoro-12,13-dihydro-5H-indolo[2,3-a]pyrrolo[3,4-c]carbazole-5,7(6H)-dione

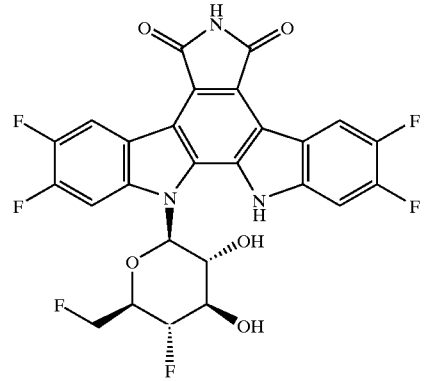

LRMS (neg. ESI, M–H$^-$) for C$_{26}$H$_{15}$F$_6$N$_3$O$_5$ m/z 562; HRMS (neg. ESI, M–H$^-$) calcd for C$_{26}$H$_{15}$F$_6$N$_3$O$_5$ m/z 562.0837; found 562.0815.

EXAMPLE 23

12-[6-Deoxy-6-[(N-methylglycinyl)amino]-β-D-glucopyranosyl]-3,9-difluoro-5H,13H-benzo[b]thienyl[2,3-a]pyrrolo[3,4-H]carbazole-5,7(6H)-dione

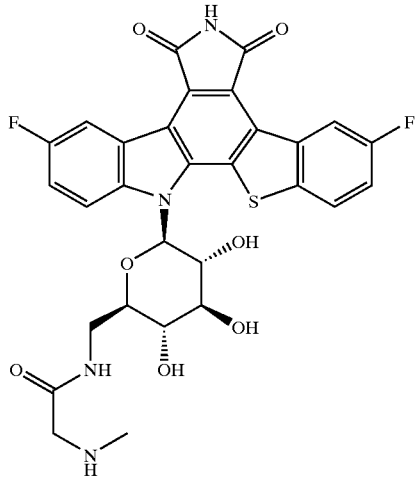

A solution of N-tert-butyloxycarbonyl-N-methylglycine (4-nitrophenyl) ester (0.150 g, 0.390 mmol) in dry THF (3 mL) was cannulated into a cold (−70° C. suspension of 12-(6-amino-6-deoxy-β-D-glucopyranosyl)-3,9-difluoro-5H,13H-benzo[b]thienyl[2,3-a]pyrrolo[3,4-c]carb-azole-5,7(6H)-dione (0.200 g, 0.369 mmol), HOBT (0.050 g, 0.369 mmol), HMPA (1.0 mL) and diisopropyl-ethytamine (0.10 mL, 1.04 mmol) in anhydrous THF (20 mL) under $N_2$. The mixture was stirred at −70 ° C. for 15 min and then at room temperature for 2.5 h. The resulting mixture was diluted with ethyl acetate, washed (saturated aqueous sodium bicarbonate, brine), dried ($Na_2SO_4$) and evaporated. Purification of the residue by flash chromatography ($SiO_2$/8% methanol-chloroform) afforded 12-[6-[[N-tert-butyloxycarbonyl-N-methylglycinyl]amino]-6-deoxy-β-D-glucopyranosyl]-3,9-difluoro-5H,13H-benzo[b]-thienyl[2,3-a]pyrrolo[3,4-c]carbazole-5,7(6H)-dione (0.231 g, 80%) as a yellow foam;

$^1$H NMR (500 MHz, DMSO-d6, rotomeric) δ 11.61 and 11.59 (2s, 1H), 9.79–9.71 (2m, 1H), 9.04–8.95 (2m, 1H), 8.32–8.28 (m, 1H), 8.09–8.03 (m, 1H), 7.96–7.92 (m, 1H), 7.58–7.51 (m,2H), 6.31 and 6.12 (d and m, J=8.9 Hz, 1H), 5.60–5.20 (br m, 3H), 4.22–3.36 (series of m, 8H), 2.72 and 2.67 (2s, 3H), 1.33, 1.11 and 1.10 (3s, 9H). IR (KBr, cm$^{-1}$) 3424, 3102, 2977, 2932, 1763, 1709, 1678, 1603, 1566, 1482, 1463, 1426, 1394, 1370, 1322, 1257, 1198, 1155, 1079, 915, 887, 807, 765, 742. MS (+ESI, M+H$^+$, M+NH$_3^+$) m/z 711 and 728.

A cold (0° C.) solution of hydrochloric acid in dioxane (4M, 5 mL) was added to a suspension of 12-[6-[[N-tert-butyloxycarbonyl-N-methylglycinyl]amino]-6-deoxy-β-D-glucopyranosyl]-3,9-difluoro-5H,13H-benzo[b]-thienyl[2,3-a]pyrrolo[3,4-c]carbazole-5,7(6H)-dione (0.095 g, 0.133 mmol) in THF (0.1 mL). The mixture was allowed to warm to room temperature over 1.5 h before it was concentrated in vacuo and diluted with diethyl ether. Filtration of the resulting suspension afforded the title compound (0.087 g, 100%) as a yellow solid, $^1$H NMR (500 MHz, DMSO-d6, rotomeric) δ 11.61 and 11.59 (2s, 1H), 9.76 and 9.71 (2dd, J=11.5, 2.5 Hz and 11.3, 2.5 Hz, 1H), 9.02 and 8.96 (2dd, J=9.7, 2.6 and 9.6, 2.7 Hz, 1H), 8.71 (br s, 1H), 8.55–8.53 (m, 1H), 8.34 and 8.28 (2dd, J=8.8, 5.2 and 8.8, 5.2 Hz, 1H), 8.09 and 8.06 (2dd, J=9.4, 4.3 and 10.4, 4.5 Hz, 1H), 7.58–7.55 (m, 1H), 7.53–7.50 (m, 1H), 6.30 and 6.13 (2d, J=8.9 and 9.4 Hz, 1H), 5.55–5.20 (series of m, 3H), 4.11–3.53 (series of m, 8H), 2.44 and 2.38 (2s, 3H). IR (KBr, cm$^{-1}$) 3412, 3070, 1745, 1702, 1686, 1623, 1602, 1567, 1481, 1464, 1426, 1324, 1258, 1196, 1077, 915, 826, 764, 742. LRMS (neg. ESI, M−H$^-$) for $C_{29}H_{24}F_2N_4O_7S$ m/z 609 and LRMS (pos. ESI, M+H$^+$) for $C_{29}H_{24}F_2N_4O_7S$ m/z 611.

EXAMPLE 24

12-[4-Deoxy-4-fluoro-β-D-glucopyranosyl]-3,9-difluoro-12,13-dihydro-5H-indolo[2,3-a]pyrrolo[3,4-c]carbazole-5,7(6H)-dione

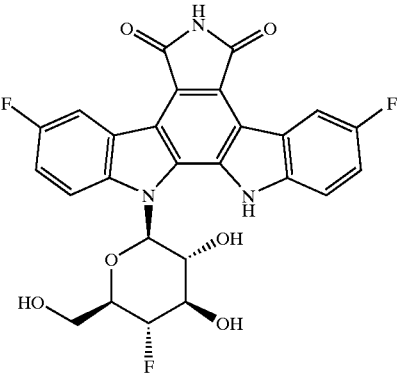

LRMS (neg. ESI, M−H$^-$) for $C_{26}H_{18}F_3N_3O_6$ m/z 524.

EXAMPLE 25

12-[4,4-Difluoro-4-deoxy-β-D-glucopyranosyl]-3,9-difluoro-12,13-dihydro-5H-indolo[2,3-a]pyrrolo[3,4-c]carbazole-5,7(6H)-dione

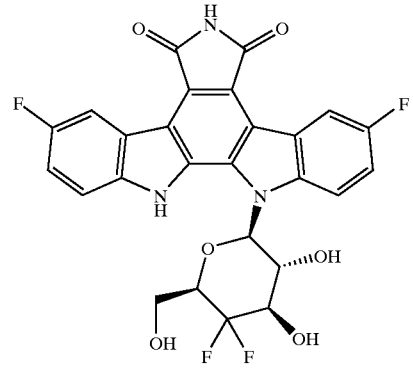

LRMS (neg. ESI, M−H$^-$) for $C_{26}H_{17}F_4N_3O_6$ m/z 542.

EXAMPLE 26

12-[4,6-Difluoro-4,6-dideoxy-β-D-glucopyranosyl]-2,3,9,10-tetrafluoro-5H,13H-benzo[b]thienyl[2,3-a]pyrrolo[3,4-c]carbazole-5,7(6H)-dione

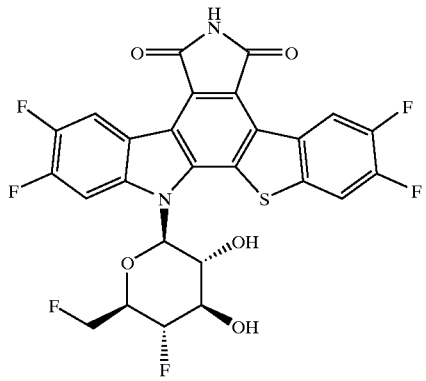

LRMS (neg. ESI, M−H⁻) for $C_{26}H_{14}F_6N_2O_5S$ m/z 579.

EXAMPLE 28

12-[4-Deoxy-4-fluoro-β-D-glucopyranosyl]-2,3,9,10-tetrafluoro-12,13-dihydro-5H-indolo[2,3-a]pyrrolo[3,4-c]carbazole-5,7(6H)-dione

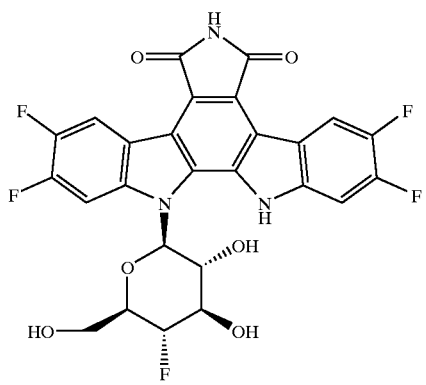

HRMS (neg. ESI, M−H⁻) calcd for $C_{26}H_{16}F_5N_3O_6$ m/z 560.08807; found 560.08660

EXAMPLE 30

12-[4,4-Difluoro-4-deoxy-β-D-glucopyranosyl]-2,3,9,10-tetrafluoro-5H,13H-benzo[b]thienyl[2,3-a]pyrrolo[3,4-c]carbazole-5,7(6H)-dione

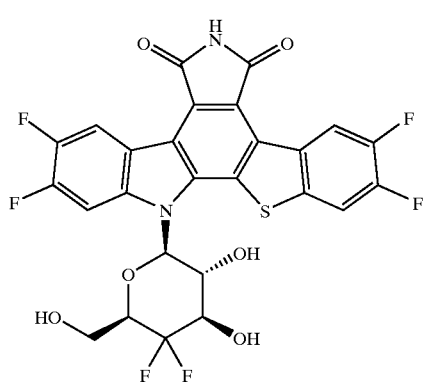

LRMS (neg. ESI, M−H⁻) for $C_{26}H_4F_6N_2O_6S$ m/z 595.

EXAMPLE 31

12-[4-Deoxy-β-D-glucopyranosyl]-3,9-difluoro-12,13-dihydro-5H-indolo[2,3-a]pyrrolo[3,4-c]carbazole-5,7(6H)-dione

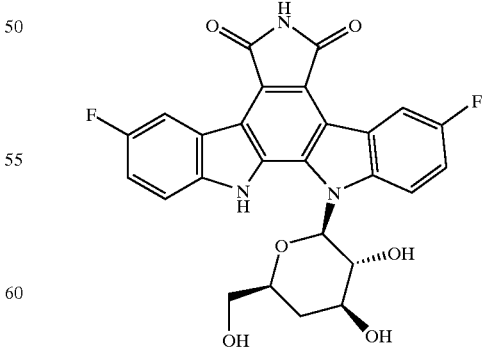

LRMS (neg. ESI, M−H⁻) for $C_{26}H_9F_2N_3O_6$ m/z 506.

EXAMPLE 32 AND 34

12-[4-Deoxy-4-fluoro-β-D-glucopyranosyl]-3,9-difluoro-12,13-dihydro-5H-indolo[2,3-a]pyrrolo[3,4-c]carbazole-5(6H)-one and 12-[4-Deoxy-4-fluoro-β-D-glucopyranosyl)-3,9-difluoro-12,13-dihydro-5H-indolo[2,3-a]pyrrolo[3,4-c]carbazole-7(6H)-one

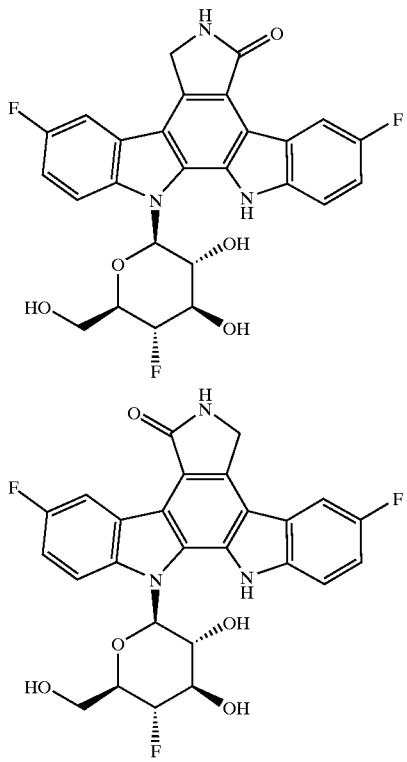

EXAMPLE 33

12-[4-Deoxy-4-fluoro-β-D-glucopyranosyl]-2,3,9,10-tetrafluoro-5H,13H-benzo[b]thienyl[2,3-a]pyrrolo[3,4-c]carbazole-5,7(6H)-dione

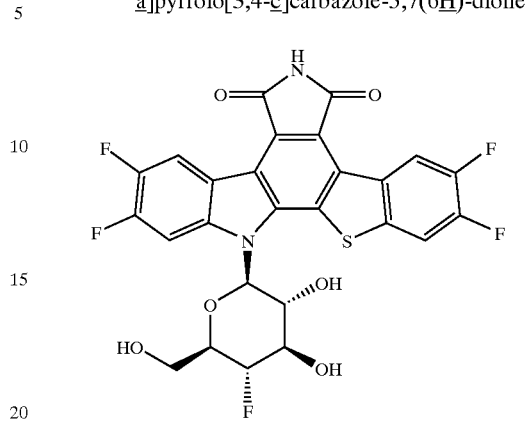

LRMS (neg. ESI, M−H⁻) for $C_{26}H_{15}F_5N_2O_6S$ m/z 577; HRMS (pos. ESI, M+H⁺) for $C_{26}H_{15}F_5N_2O_6S$ m/z 579.064226; found 579.06420.

What is claimed is:

1. A compound of formula I

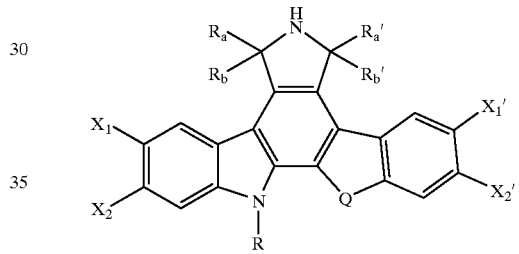

having a topoisomerase I selectivity index of greater than about 100; its enantiomers, diastereomers, pharmaceutically acceptable salts, hydrates, prodrugs and solvates thereof; wherein $R_a$ and $R_b$ are independently selected from the group consisting of H and O, provided that when O is selected $R_a$ and $R_b$ are taken together to form O; $R_a'$ and $R_b'$ are independently selected from the group consisting of H and O, provided that when O is selected $R_a'$ and $R_b'$ are taken together to form O; $X_1$, $X_1'$, $X_2$ and $X_2'$ are each independently selected from the group consisting of F, Br and H; Q is selected from the group consisting of NH, S and O; and R is a substituted hexose group, wherein said hexose group is substituted with one of:

(a) a fluoro (F) or an azido ($N_3$) at the 3-position and one of an alkoxy, an alkylhalo, and a cyanamide at the 4-position; or (b) a hydroxyl (OH) at the 3-position and one of an alkyl, a carboxylic acid, an alkylamino, an alkylmorpholino, an alkylthiol, an alkoxy, an alkylnitro and a nitro at the 4-position.

2. The compound according to claim 1 wherein $X_1$ is F; $X_1'$ is selected from the group consisting of F and Br; and $X_2$ and $X_2'$ are selected from the group consisting of F and H, and wherein:

(a) when said substituted hexose includes a fluoro (F) or an azido ($N_3$) at the 3-position, said hexose is further substituted with one of $CH_2OH$, $CH_2F$ and $CH_2N_2$ at the 4-position; and To a solution of 12-[4-deoxy-4-fluoro-β-D-glucopyranosyl]-3,9-difluoro-12,13-dihydro-5H-indolo[2,3-a]pyrrolo[3,4-c]carbazole-5,7(6H)-dione (0.180 g, 0.34 mmole) in 11 mL of ethanol-THF (10:1) was added NaBH₄ (0.065 g, 1.7 mmol) all at once and the mixture was stirred at room temperature under Ar for 4 days. The resulting mixture was diluted with EtOAc, washed (saturated aqueous NH₄Cl, brine), dried (Na₂SO₄) and evaporated. The resulting pale yellow solid was taken up in 10 mL of dry THF and then p-toluenesulfonic acid monohydrate (0.007 g) and phenylselenol (0.253 mL, 2.38 mmol) were added. The reaction mixture was stirred at room temperature until the reaction was complete by tlc and then the mixture was evaporated to dryness. The residue was triturated with ether and the ether-insoluble fraction was purified by column chromatography (Sephadex LH-20/methanol) to give two major fractions. Fraction 1 was identified as 12-[4-deoxy-4-fluoro-β-D-glucopyranosyl]-3,9-difluoro-12,13-dihydro-5H-indolo[2,3-a]pyrrolo[3,4-c]carbazole-7(6H)-one;

LRMS (neg. ESI, M−H⁻) for $C_{26}H_{20}F_3N_3O_5$ m/z 510.

Fraction 2 was identified as 12-[4-deoxy-4-fluoro-β-D-glucopyranosyl]-3,9-difluoro-12,13-dihydro-5H-indolo[2,3-a]pyrrolo[3,4-c]carbazole-5(6H)-one;

LRMS (neg. ESI, M−H⁻) for $C_{26}H_{20}F_3N_3O_5$ m/z 510.

(b) when said substituted hexose includes a hydroxyl (OH) at the 3-position, said hexose is further substituted with one of CH$_2$F, CH$_2$NH$_2$, CH$_2$SOCH$_3$, CH$_2$-morphilino, CH$_2$OH, and CH$_2$NHCOCH$_2$NHCH$_3$ at the 4-position.

3. The compound according to claim 1 wherein X$_1$ and X$_1$' are F; X$_2$ and X$_2$' are H; Q is NH; R$_a$ and R$_b$ are taken together to form O; and R$_a$' and R' are taken together to form O.

4. A compound of formula I

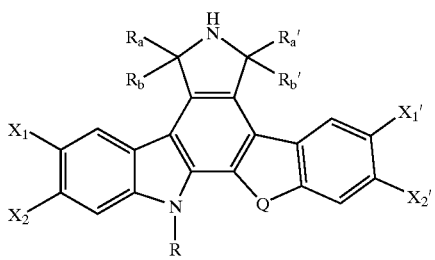

having a topoisomerase I selectivity index of greater than about 100; its enantiomers, diastereomers, pharmaceutically acceptable salts, hydrates, prodrugs and solvates thereof; wherein R$_a$ and R$_b$ are independently selected from the group consisting of H and O, provided that when O is selected R$_a$ and R$_b$ are taken together to form O; R$_a$' and R$_b$' are independently selected from the group consisting of H and O, provided that when O is selected R$_a$' and R$_b$' are taken together to form O; X$_1$ and X$_1$' are F, X$_2$ and X$_2$' are each independently selected from the group consisting of F, Br and H; Q is selected from the group consisting of NH, S and O; and R is a substituted hexose group wherein X$_1$ and X$_1$' are F; X$_2$ and X$_2$' are H; Q is NH; R$_a$ and R$_b$ are taken together as O; R$_a$' and R$_b$' are H; and said substituted hexose group is

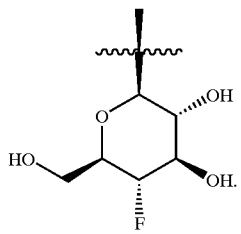

5. A compound of formula I

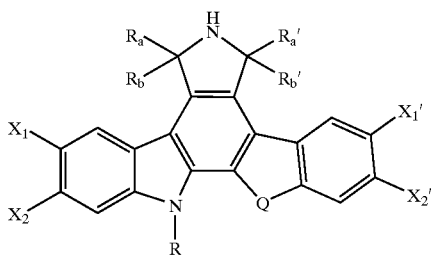

having a topoisomerase I selectivity index of greater than about 100; its enantiomers, diastereomers, pharmaceutically acceptable salts, hydrates, prodrugs and solvates thereof; wherein R$_a$ and R$_b$ are independently selected from the group consisting of H and O, provided that when O is selected R$_a$ and R$_b$ are taken together to form O; R$_a$' and R$_b$' are independently selected from the group consisting of H and O, provided that when O is selected R$_a$' and R$_b$' are taken together to form O; X$_1$ and X$_1$' are F, X$_2$ and X$_2$' are each independently selected from the group consisting of F, Br and H; Q is selected from the group consisting of NH, S and O; and R is a substituted hexose group wherein X$_1$ and X$_1$' are F; X$_2$ and X$_2$' are H; Q is NH; R$_a$' and R$_b$' are taken together as O; R$_a$ and R$_b$ are H; and said substituted hexose group is

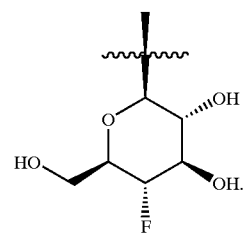

6. A compound of formula I

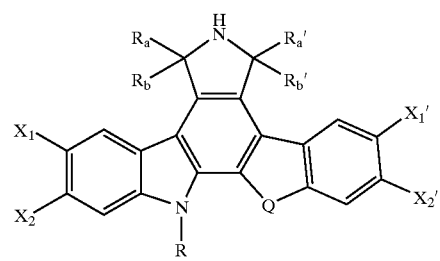

having a topoisomerase I selectivity index of greater than about 100; its enantiomers, diastereomers, pharmaceutically acceptable salts, hydrates, prodrugs and solvates thereof; wherein R$_a$ and R$_b$ are independently selected from the group consisting of H and O, provided that when O is selected R$_a$ and R$_b$ are taken together to form O; R$_a$' and R$_b$' are independently selected from the group consisting of H and O, provided that when O is selected R$_a$' and R$_b$' are taken together to form O; X$_1$ and X$_1$' are F, X$_2$ and X$_2$' are each independently selected from the group consisting of F, Br and H; Q is selected from the group consisting of NH, S and O; and R is a substituted hexose group wherein X$_1$, X$_1$', X$_2$ and X$_2$' are F; Q is S; R$_a$ and R$_b$ are taken together to form O; R$_a$' and R$_b$' are taken together to form O; and said substituted hexose group is

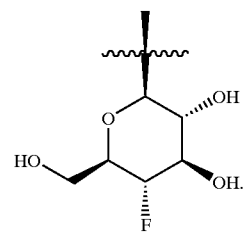

7. The compound according to claim 1 wherein X$_1$ and X$_1$' are F; X$_2$ and X$_2$' are H; Q is NH; R$_a$ and R$_b$ are taken together to form O; R$_a$' and R$_b$' are taken together to form O; and said substituted hexose group is

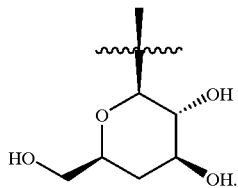

8. The compound according to claim 1 wherein $X_1$, $X_1'$, $X_2$ and $X_2'$ are F; Q is S; $R_a$ and $R_b$ are taken together to form O; $R_a'$ and $R_b'$ are taken together to form O; and said substituted hexose group is

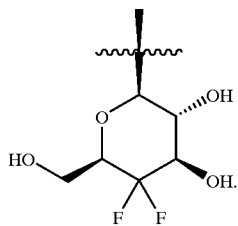

9. The compound according to claim 1 wherein $X_1$, $X_1'$, $X_2$ and $X_2$ are F; Q is NH; $R_a$ and $R_b$ are taken together to form O; $R_a'$ and $R_b'$ are taken together to form O; and said substituted hexose group is

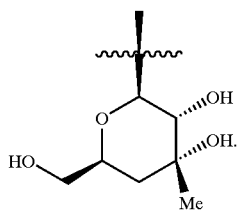

10. A compound of formula I

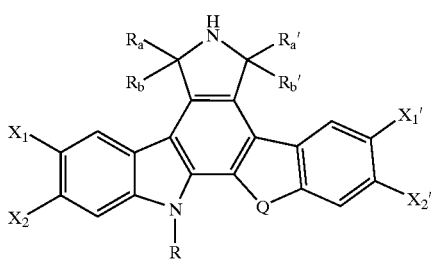

having a topoisomerase I selectivity index of greater than about 100; its enantiomers, diastereomers, pharmaceutically acceptable salts, hydrates, prodrugs and solvates thereof; wherein $R_a$ and $R_b$ are independently selected from the group consisting of H and O, provided that when O is selected $R_a$ and $R_b$ are taken together to form O; $R_a'$ and $R_b'$ are independently selected from the group consisting of H and O, provided that when O is selected $R_a'$ and $R_b'$ are taken together to form O; $X_1$ and $X_1'$ are F, $X_2$ and $X_2'$ are each independently selected from the group consisting of F, Br and H; Q is selected from the group consisting of NH, S and O; and R is a substituted hexose group wherein $X_1$, $X_1'$, $X_2$ and $X_2'$ are F; Q is NH; $R_a$ and $R_b$ are taken together to form O; $R_a'$ and $R_b'$ are taken together to form O; and said substituted hexose group is

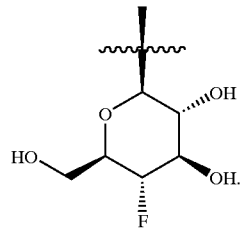

11. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

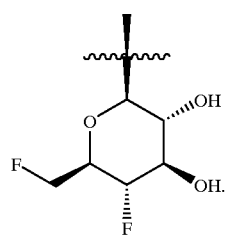

12. The compound according to claim 1 wherein $X_1$, $X_1'$, $X_2$ and $X_2'$ are F; Q is S; $R_a$ and $R_b$ are taken together to form O; $R_a'$ and $R_b'$ are taken together to form O; and said substituted hexose group is

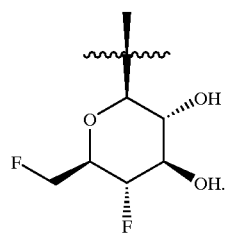

13. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

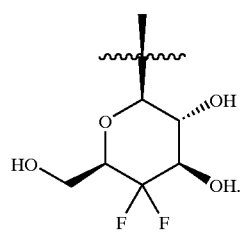

14. The compound according to claim 1 wherein $X_1$ and $X_1'$ are F; $X_2$ and $X_2'$ are H; Q is S; $R_a$ and $R_b$ are taken together to form O; $R_a'$ and $R_b'$ are taken together to form O; and said substituted hexose group is

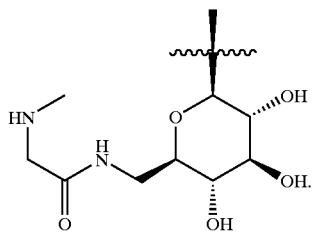

15. The compound according to claim 1 wherein $X_1$, $X_1'$, $X_2$ and $X_2'$ are F; Q is NH; $R_a$ and $R_b$ are taken together to form O; $R_a'$ and $R_b'$ are taken together to form O; and said substituted hexose group is

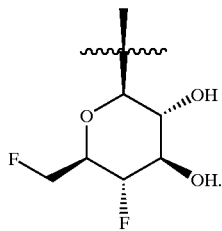

16. The compound according to claim 1 wherein $X_1$, $X_1'$, $X_2$ and $X_2'$ are F; Q is NH; $R_a$ and $R_b$ are taken together to form O; $R_a'$ and $R_b'$ are taken together to form O; and said substituted hexose group is

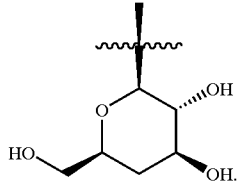

17. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

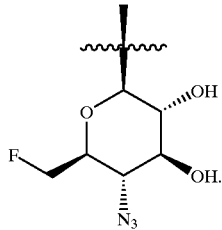

18. The compound according to claim 1 wherein $X_1$, $X_1'$, $X_2$ and $X_2'$ are F; Q is NH; $R_a$ and $R_b$ are taken together to form O; $R_a'$ and $R_b'$ are taken together to form O; and said substituted hexose group is

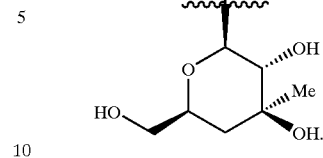

19. The compound according to claim 1 wherein $X_1$, $X_1'$, $X_2$ and $X_2'$ are F; Q is NH; $R_a$ and $R_b$ are taken together to form O; $R_a'$ and $R_b'$ are taken together to form O; and said substituted hexose group is

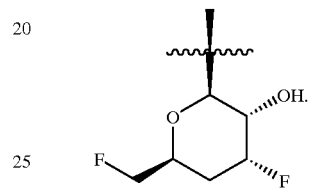

20. The compound according to claim 1 wherein $X_1$ is F; $X_1'$ is Br; $X_2$ and $X_2'$ are H; Q is O; $R_a$ and $R_b$ are taken together to form O; $R_a'$ and $R_b'$ are taken together to form O; and said substituted hexose group is

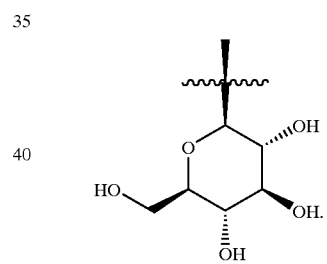

21. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

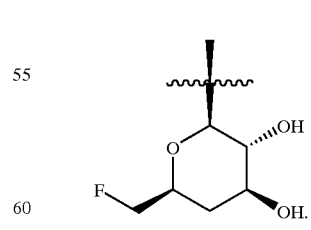

22. The compound according to claim 1 wherein $X_1$, $X_1'$, $X_2$ and $X_2'$ are F; Q is NH; $R_a$ and $R_b$ are taken together to form O; $R_a'$ and $R_b'$ are taken together to form O; and said substituted hexose group is

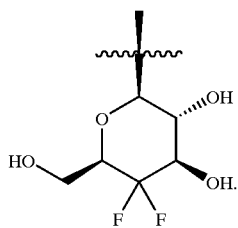

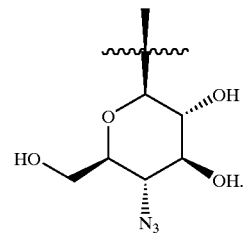

23. The compound according to claim 1 wherein $X_1$ and $X_1'$ are F $X_2$ and $X_2'$ are H; Q is S; $R_a$ and $R_b$ are taken together to form O; $R_a'$ and $R_b'$ are taken together to form O; and said substituted hexose group is

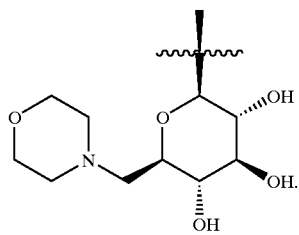

24. The compound according to claim 1 wherein $X_1$, $X_1'$, $X_2$ and $X_2'$ are F; Q is S; $R_a$ and $R_b$ are taken together to form O; $R_a'$ and $R_b'$ are taken together to form O; and said substituted hexose group is

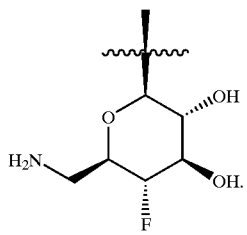

25. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

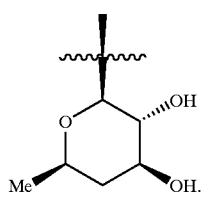

26. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

27. The compound according to claim 1 wherein $X_1$, $X_1'$, $X_2$ and $X_2'$ are F; Q is S; $R_a$ and $R_b$ are taken together to form O; $R_a'$ and $R_b'$ are taken together to form O; and said substituted hexose group is

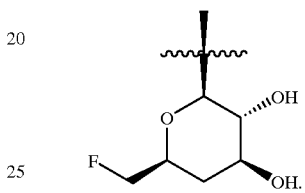

28. The compound according to claim 1 wherein $X_1$, $X_1'$, $X_2$ and $X_2'$ are F; Q is S; $R_a$ and $R_b$ are taken together to form O; $R_a'$ and $R_b'$ are taken together to form O; and said substituted hexose group is

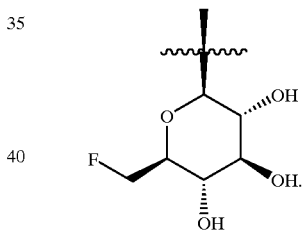

29. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

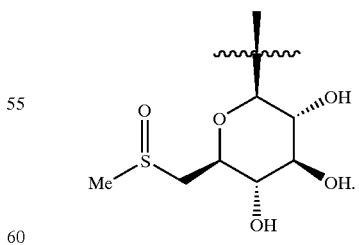

30. The compound according to claim 1 wherein $X_1$ and $X_1'$ are F; $X_2$ and $X_2'$ are H; Q is S; $R_a$ and $R_b$ are taken together to form O; $R_a'$ and $R_b'$ are taken together to form O; and said substituted hexose group is

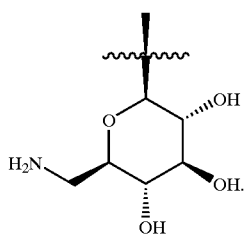

31. The compound according to claim 1 wherein $X_1$, $X_1'$, $X_2$ and $X_2'$ are F; Q is NH; $R_a$ and $R_b$ are taken together to form O; $R_a'$ and $R_b'$ are taken together to form O; and said substituted hexose group is

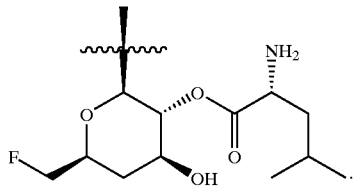

32. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

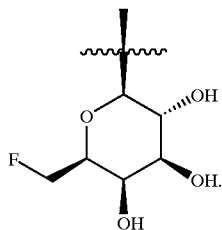

33. The compound according to claim 1 wherein $X_1$ and $X_1'$ are F; $X_2$ and $X_2'$ are H; Q is S; $R_a$ and $R_b$ are taken together to form O; $R_a'$ and $R_b'$ are taken together to form O; and said substituted hexose group is

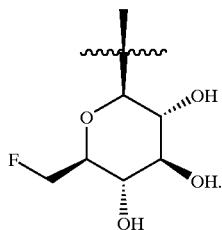

34. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

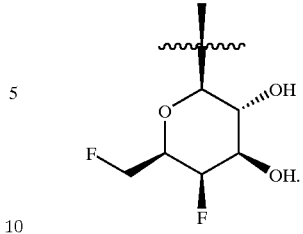

35. The compound according to claim 1 wherein $X_1$ and $X_1'$ are F; $X_2$ and $X_2'$ are H; Q is NH; $R_a$ and $R_b$ are taken together to form O; $R_a'$ and $R_b'$ are taken together to form O; and said substituted hexose group is

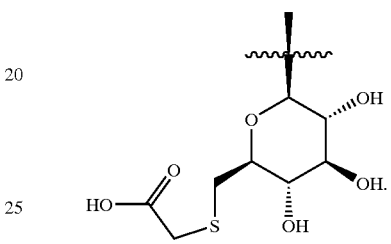

36. The compound according to claim 1 wherein said topoisomerase I selectivity index is greater than about 1000.

37. The compound

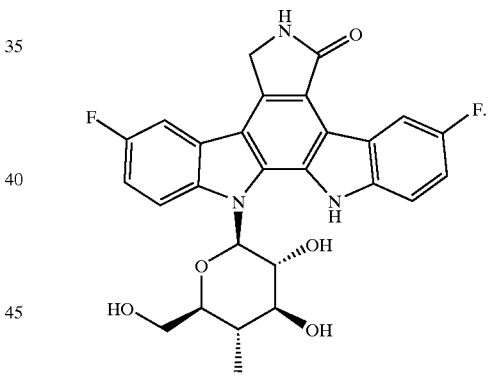

38. The compound

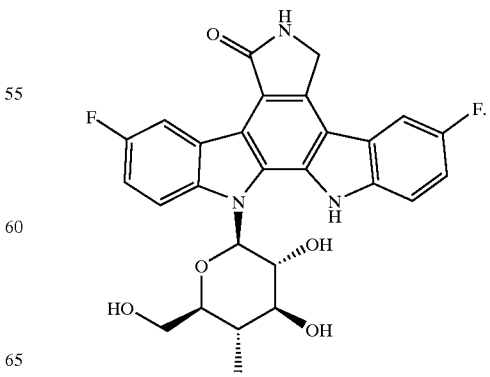

39. The compound

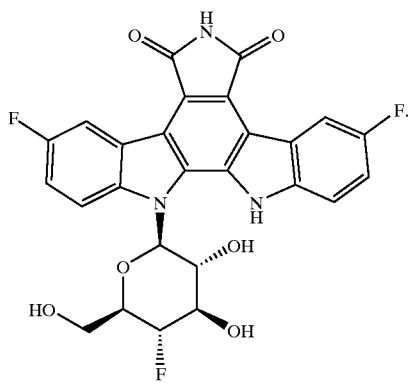

40. A method for treating a condition via modulation of topoisomerase I comprising administering to a mammalian species in need of such treatment an effective amount of at least one compound of formula I as claimed in claim 1.

41. The method according to claim 8 wherein the condition is cancer.

42. The method of claim 9 further comprising administering to said mammalian species at least one other anti-cancer agent in combination.

43. A method for treating a condition via modulation of topoisomerase I comprising administering to a mammalian species in need of such treatment an effective amount of at least one compound of formula I as claimed in claim 1.

44. A compound of formula (I), having a topoisomerase I selectivity index of greater than about 100, its enantiomers, diastereomers, pharmaceutically acceptable salts, hydrates, prodrugs and solvates thereof, wherein said compound is one or more of the group consisting of compounds 1 through to 34.

45. A method for treating a condition via modulation of topoisomerase I comprising administering to a mammalian species in need of such treatment an effective amount of at least one compound of formula I as claimed in claim 44.

* * * * *

UNITED STATES PATENT AND TRADEMARK OFFICE
CERTIFICATE OF CORRECTION

PATENT NO.     : 6,855,698 B2
DATED          : February 15, 2005
INVENTOR(S)    : Ruediger et al.

It is certified that error appears in the above-identified patent and that said Letters Patent is hereby corrected as shown below:

Title page,
Item [75], Inventors, "Balusubramanian" should be replaced with
-- Balasubramanian --;

Column 56,
Lines 53, 56 and 65, "3-position" should be replaced with -- 4-position --;
Lines 53-54, "one of an alkoxy," should be deleted;
Line 54, ", and a cyanamide" should be deleted;
Lines 55, 59 and 67, "4-position" should be replaced with -- 5-position --;
Line 57, "a carboxylic acid," should be deleted;
Lines 57-58, -- and -- should be inserted between "alkylmorpholino," and "an alkylthiol";
Line 58, ", an alkoxy, an alkylnitro and a nitro" should be deleted;
Line 66, "," between "CH$_2$OH" and "CH$_2$F" and "and CH$_2$N$_2$" should both be deleted; and -- and -- should be inserted between "CH$_2$OH" and "CH$_2$F";

Column 57,
Line 2, "3-position" should be replaced with -- 4-position --;
Line 4, "morphilino" should be replaced with -- morpholino --;
Line 5, "4-position" should be replaced with -- 5-position --.

Signed and Sealed this

Second Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 6,855,698 B2  Page 1 of 1
APPLICATION NO. : 10/103908
DATED : February 15, 2005
INVENTOR(S) : Edward H. Ruediger et al.

It is certified that error appears in the above-identified patent and that said Letters Patent is hereby corrected as shown below:

Column 56,
Lines 53, 56 and 65, "4-position" should be replaced with --3-position--.
Lines 53-54, after "and" insert --one of an alkoxy--.
Line 54, after "alkylhalo" insert --, and a cyanamide--.
Lines 55, 59 and 67, "5-position" should read --4-position--.
Line 57, before "alkylamino" insert --a carboxylic acid,--.
Lines 57-58, delete the word "and" between "alkylmorpolino" and "an alkylthiol".
Line 58, after "alkylthiol" insert --an alkoxy, an alkylnitro and a nitro--.
Line 66, should read --substituted with one of $CH_2OH$, $CH_2F$ and $CH_2N_2$ at--.

Column 57,
Line 2, "4-position" should be replaced with --3-position--.
Line 4, "morpholino" should read --morphilino--.
Line 5, "5-position" should read --4-position--.

Signed and Sealed this

Eleventh Day of July, 2006

JON W. DUDAS
*Director of the United States Patent and Trademark Office*

UNITED STATES PATENT AND TRADEMARK OFFICE
CERTIFICATE OF CORRECTION

PATENT NO. : 6,855,698 B2 Page 1 of 1
APPLICATION NO. : 10/103908
DATED : February 15, 2005
INVENTOR(S) : Edward H. Ruediger et al.

It is certified that error appears in the above-identified patent and that said Letters Patent is hereby corrected as shown below:

This certificate supersedes Certificate of Correction issued May 2, 2006 and July 11, 2006. The certificates were issued in error and should be deleted. The corrections are inconsistent with the prior decision from the PTO dated April 18, 2005 denying the changes in the claims since the changes would require reexamination.

Title Page

Item (75) Inventors, "Balusubramanian" should read --.Balasubramanian--.

Signed and Sealed this

Twelfth Day of December, 2006

JON W. DUDAS
*Director of the United States Patent and Trademark Office*